United States Patent
Aman et al.

(10) Patent No.: US 10,487,140 B2
(45) Date of Patent: Nov. 26, 2019

(54) TARGETING IMMUNOLOGICAL FUNCTIONS TO THE SITE OF BACTERIAL INFECTIONS USING CELL WALL TARGETING DOMAINS OF BACTERIOLYSINS

(71) Applicant: INTEGRATED BIOTHERAPEUTICS, INC., Gaithersburg, MD (US)

(72) Inventors: Mohammad Javad Aman, Rockville, MD (US); Rajan Prasad Adhikari, Gaithersburg, MD (US)

(73) Assignee: INTEGRATED BIOTHERAPEUTICS, INC., Rockville, MD (US)

( * ) Notice: Subject to any disclaimer, the term of this patent is extended or adjusted under 35 U.S.C. 154(b) by 68 days.

(21) Appl. No.: 15/111,383

(22) PCT Filed: Jan. 14, 2015

(86) PCT No.: PCT/US2015/011455
§ 371 (c)(1),
(2) Date: Jul. 13, 2016

(87) PCT Pub. No.: WO2015/109012
PCT Pub. Date: Jul. 23, 2015

(65) Prior Publication Data
US 2016/0333077 A1    Nov. 17, 2016

Related U.S. Application Data

(60) Provisional application No. 61/927,120, filed on Jan. 14, 2014.

(51) Int. Cl.
*C07K 16/12* (2006.01)
*C07K 14/195* (2006.01)
*C12N 9/52* (2006.01)
*A61K 38/00* (2006.01)

(52) U.S. Cl.
CPC ........ *C07K 16/1271* (2013.01); *C07K 14/195* (2013.01); *C12N 9/52* (2013.01); *C12Y 304/24075* (2013.01); *A61K 38/00* (2013.01); *C07K 2317/24* (2013.01); *C07K 2317/76* (2013.01); *C07K 2319/00* (2013.01); *C07K 2319/70* (2013.01)

(58) Field of Classification Search
None
See application file for complete search history.

(56) References Cited

U.S. PATENT DOCUMENTS

2009/0087478 A1    4/2009   Hansen et al.

FOREIGN PATENT DOCUMENTS

| JP | 2006504619 A | 2/2006 | |
| JP | 2012509259 A | 4/2012 | |
| WO | 1997/08553 A1 | 3/1997 | |
| WO | WO-9708553 A1 * | 3/1997 | ............. C12N 15/62 |
| WO | WO-2004110143 A2 * | 12/2004 | ............. A01N 63/00 |
| WO | 2008/011157 A2 | 1/2008 | |
| WO | 2010/085682 A2 | 7/2010 | |
| WO | 2012/109167 A1 | 8/2012 | |
| WO | 2012/109285 A2 | 8/2012 | |
| WO | 2013135588 A1 | 9/2013 | |
| WO | 2013138795 A1 | 9/2013 | |

OTHER PUBLICATIONS

Walls et al., J. Med. Microbiol., 52:829-833, 2003.*
Baylor et al (Vaccine, 20:S18-S23, 2002).*
Ahmed et al., "Evaluation of Cell Wall Binding Domain of *Staphylococcus aureus* Autolysin as Affinity Reagent for Bacteria and its Application to Bacterial Detection", Journal of Bioscience and Bioengineering, 2007, pp. 55-61, vol. 104, No. 4.
Baba et al., "Target Cell Specificity of a Bacteriocin Molecule: A C-Terminal Signal Directs Lysostaphin to the Cell Wall of *Staphylococcus aureus*", The EMBO Journal, Sep. 16, 1996, pp. 4789-4797, vol. 15 No. 18.
Baba et al., "Targeting of Muralytic Enzymes to the Cell Division Site of Gram-Positive Bacteria: Repeat Domains Direct Autolysin to the Equatorial Surface Ring of *Staphylococcus aureus*", The EMBO Journal, Aug. 17, 1998, pp. 4639-4646, vol. 17, Issue 16.
Catalão et al., "The Endolysin-Binding Domain Encompasses the N-Terminal Region of the Mycobacteriophage Ms6 Gp1 Chaperone" Journal of Bacteriology, Sep. 2011, pp. 5002-5006, vol. 193, No. 18.
Cohen et al., "Phage Therapy Treatment of the Coral Pathogen *Vibrio coralliilyticus*", Microbiology Open, Feb. 2013, pp. 64-74, vol. 2, Issue 1.
Cruz et al., "Bacteriocin AS-48 Binding to Model Membranes and Pore Formation as Revealed by Coarse-Grained Simulations", BBA Biomembranes, Nov. 2013, pp. 2524-2531, vol. 1828, Issue 11.
Daniel et al., "Synergism between a Novel Chimeric Lysin and Oxacillin Protects against Infection by Methicillin-Resistant *Staphylococcus aureus*". Antimicrobial Agents and Chemotherapy, Apr. 2010, pp. 1603-1612, vol. 54, Issue 4.
Donovan et al., "Peptidoglycan Hydrolase Fusions Maintain Their Parental Specificities", Applied and Environmental Microbiology, Apr. 2006, pp. 2988-2996, vol. 72, No. 4.
Díez-Martínez et al., "Improving the Lethal Effect of Cpl-7, a Pneumococcal Phage Lysozyme with Broad Bactericidal Activity, by Inverting the Net Charge of Its Cell Wall-Binding Module", Antimicrobial Agents and Chemotherapy, Nov. 2013, pp. 5355-5365, vol. 57, No. 11.

(Continued)

*Primary Examiner* — Brian Gangle
(74) *Attorney, Agent, or Firm* — Thompson Coburn LLP; William A. Holtz

(57) ABSTRACT

This disclosure provides a comprehensive approach to specifically target various immune functions to the site of infection by a variety of fusion proteins that consist of a bacteriocin cell wall targeting domain (CWT) and an immune function mediating component (IFMC). The CWT targets the fusion protein to the bacterial surface leading to accumulation at the site of infection. The IFMC mediates various immune functions such as toxin neutralization or recruitment of immune cells that can clear the bacteria.

**27 Claims, 6 Draw

(56) References Cited

OTHER PUBLICATIONS

Fritz et al., "A Serologic Correlate of Protective Immunity Against Community-Onset *Staphylococcus aureus* Infection", Clincial Infectious Disease, Jun. 1, 2013, pp. 1554-1561, vol. 56, Issue 11.
Ganguly et al., "The Secondary Cell Wall Polysaccharide of Bacillus Anthracis Provides the Specific Binding Ligand for the C-Terminal Cell Wall-Binding Domain of Two Phage Endolysins, PlyL and PlyG" Glycobiology, Jul. 2013, pp. 820-832, vol. 23, Issue 7.
Gilmer et al., "Novel Bacteriophage Lysin with Broad Lytic Activity Protects against Mixed Infection by *Streptococcus pyogenes* and Methicillin-Resistant *Staphylococcus aureus*", Antimicrobial Agents and Chemotherapy, Jun. 2013, pp. 2743-2750, vol. 57, No. 6.
Grundling et al., "Cross-Linked Peptidoglycan Mediates Lysostaphin Binding to the Cell Wall Envelope of *Staphylococcus aureus*", Journal of Bacteriology, Apr. 1, 2006, pp. 2463-2472, vol. 188 No. 7.
Hahn et al., "Pilin-Based Anti-Pseudomonas Vaccines: Latest Developments and Perspectives", Behring Institute Mitteilungen, Feb. 1997, pp. 315-325, vol. 98.
Horgan et al., "Phage Lysin LysK Can Be Truncated to Its CHAP Domain and Retain Lytic Activity against Live Antibiotic-Resistant Staphylococci", Applied and Environmental Microbiology, Feb. 2009, pp. 872-874, vol. 75, No. 3.
Housden et al., "Directed Epitope Delivery Across the *Escherichia coli* Outer Membrane Through the Porin OmpF", Proceedings of the National Academy of Sciences USA, Dec. 14, 2010, pp. 21412-21417, vol. 107, No. 50.
International Search Report and Written Opinion for PCT/US2015/011455 dated May 6, 2015.
Komatsuzawa et al., "Subcellular Localization of the Major Autolysin, ATL and Its Processed Proteins in *Staphylococcus aureus*", Microbiology and Immunology, Jun. 1997, pp. 469-479, vol. 41, Issue 6.
Loessner et al., "C-Terminal Domains of Listeria monocytogenes Bacteriophage Murein Hydrolases Determine Specific Recognition and High-Affinity Binding to Bacterial Cell Wall Carbohydrates", Molecular Biology, Apr. 2002, pp. 335-349, vol. 44, Issue 2.
Lukacik et al., "Structural Engineering of a Phage Lysin that Targets Gram-Negative Pathogens", Proceedings of the National Academy of Sciences USA, Jun. 19, 2012, pp. 9857-9862, vol. 106, No. 25.
Manoharadas et al., "Antimicrobial Activity of a Chimeric Enzybiotic Towards *Staphylococcus aureus*", Journal of Biotechnology, Jan. 1, 2009, pp. 118-123, vol. 139, Issue 1.
Mayer et al., "Molecular Characterization of a Clostridium difficile Bacteriophage and Its Cloned Biologically Active Endolysin", Journal of Bacteriology, Oct. 2008, pp. 6734-6740, vol. 190, No. 20.
Mayer et al., "Structure-Based Modification of a Clostridium difficile-Targeting Endolysin Affects Activity and Host Range ", Journal of Bacteriology, Oct. 2011, pp. 5477-5486, vol. 193, No. 19.
Mohanty et al., "Enzymatic E-colicins Bind to Their Target Receptor BtuB by Presentation of a Small Binding Epitope on a Coiled-coil Scaffold", Journal of Biological Chemistry, Oct. 17, 2003, pp. 40953-40958, vol. 278, Issue 42.
Nelson et al., "Prevention and Elimination of Upper Respiratory Colonization of Mice by Group A Streptococci by Using a Bacteriophage Lytic Enzyme", Proceedings of the National Academy of Sciences, Mar. 27, 2001, pp. 4107-4112, vol. 98, No. 7.
Oshida et al., "A *Staphylococcus aureus* Autolysin that has an N-Acetylmuramoyl-L-Alanine Amidase Domain and an Endo-Beta-N-Acetylglucosaminidase Domain: Cloning, Sequence Analysis, and Characterization", Proceedings of the National Academy of Sciences, Jan. 3, 1995, pp. 285-289, vol. 92, No. 1.

Paradis-Bleau et al., "Peptidoglycan Lytic Activity of the Pseudomonas Aeruginosa Phage ÅKZ gp144 Lytic Transglycosylase", FEMS Microbiology Letters, Jan. 2007, pp. 201-209, vol. 266, Issue 2.
Penfold et al., "Flexibility in the Receptor-Binding Domain of the Enzymatic Colicin E9 Is Required for Toxicity against *Escherichia coli* Cells", Journal of Bacteriology, Jul. 2004, pp. 4520-4527, vol. 186, Issue 14.
Portrait et al., "A Fusobacterium Mortiferum Strain Produces a Bacteriocin-Like Substance(s) Inhibiting *Salmonella enteritidis*", Letters in Applied Microbiology, Aug. 2000, pp. 115-117, vol. 31, Issue 2.
Prasad et al., "A Novel Bacteriocin-Like Substance (BLIS) From a Pathogenic Strain of Vibrio harveyi", Microbiology, Sep. 2005, pp. 3051-3058, vol. 151, Issue 9.
Rashel et al., "Efficient Elimination of Multidrug-Resistant *Staphylococcus aureus* by Cloned Lysin Derived from Bacteriophage fMR11", The Journal Infectious Diseases, Oct. 15, 2007, pp. 1237-1247, vol. 196, Issue 8.
Sabala et al., "Anti-Staphylococcal Activities of Lysostaphin and LytM Catalytic Domain", BMC Microbiology, Jun. 6, 2012, vol. 12, No. 97.
Sass et al., "Lytic Activity of Recombinant Bacteriophage j11 and j12 Endolysins on Whole Cells and Biofilms of *Staphylococcus aureus*" Applied and Environmental Microbiology, Jan. 2007, pp. 347-352, vol. 73, vol. 1.
Satishkumar et al., "Antibody-directed Targeting of Lysostaphin Adsorbed onto Polylactide Nanoparticles Increases its Antimicrobial Activity Against *S. aureus* In Vitro; Antibody-directed Targeting of Lysostaphin Adsorbed onto Polylactide Nanoparticles Increases its Antimicrobial Activity Against *S. aureus* In Vitro", Nanotechnology, Nov. 23, 2011, pp. 505103, vol. 22 No. 50.
Seo et al., "Characterization of the Fibrinogen Binding Domain of Bacteriophage Lysin from *Streptococcus mitis*", Infection and Immunity, Sep. 2011, pp. 3518-3526, vol. 79, No. 9.
Sivadon et al., "Polymorphism of the Cell Wall-Anchoring Domain of the Autolysin-Adhesin AtlE and Its Relationship to Sequence Type, as Revealed by Multilocus Sequence Typing of Invasive and Commensal *Staphylococcus epidermidis* Strains", Journal of Clinical Microbiology, May 2006, pp. 1839-1843, vol. 44, No. 5.
Sycheva et al., "Crystal Structure and Location of gp131 in the Bacteriophage phiKZ Virion", Virology, Dec. 20, 2012, pp. 257-264, vol. 434, Issue 2.
Takac et al., "Phage P68 Virion-Associated Protein 17 Displays Activity against Clinical Isolates of *Staphylococcus aureus*", Antimicrobial Agents and Chemotherapy, Jul. 2005, pp. 2934-2940, vol. 49, No. 7.
Vipra et al., "Antistaphylococcal Activity of Bacteriophage Derived Chimeric Protein P128", BMC Microbiology, Mar. 22, 2012, vol. 12, No. 41.
Walmagh et al., "Characterization of Modular Bacteriophage Endolysins from Myoviridae Phages OBP, 201f2-1 and PVP-SE1", PLoS One, May 15, 2012, pp. e36991, vol. 7, No. 5.
Wang et al., "Holins: The Protein Clocks of Bacteriophage Infections", Annual Review of Microbiology, Oct. 2000, pp. 799-825, vol. 54.
Wang et al., "Sizing the Holin Lesion with an Endolysin-b-Galactosidase Fusion", Journal of Bacteriology, Feb. 2003, pp. 779-787, vol. 185, Issue 3.
Wang et al., "Therapeutic Effectiveness of Bacteriophages in the Rescue of Mice with Extended Spectrum b-Lactamase-Producing *Escherichia coli* Bacteremia", International Journal of Molecular Medicine, Feb. 1, 2006, pp. 347-355, vol. 17, No. 2.

\* cited by examiner

TARGETING IMMUNOLOGICAL FUNCTIONS TO THE SITE OF BACTERIAL INFECTIONS USING CELL WALL TARGETING DOMAINS OF BACTERIOLYSINS

CROSS-REFERENCE TO RELATED APPLICATIONS

This patent application is a 35 U.S.C. § 371 National Phase Application of International Patent Application No. PCT/US2015/011455, filed Jan. 14, 2015, and incorporated herein by reference in its entirety, which claims priority to U.S. Provisional Application No. 61/927,120, filed Jan. 14, 2014, which is incorporated herein in its entirety.

BACKGROUND

Bacteriolysins, including phage-encoded lysins and bacteriocins are enzymes that target one of the four major cell wall peptidoglycan bonds leading to lysis of the bacterial cell wall. Lysins accumulate in the cytoplasm of infected bacteria during phage life cycle. At a genetically hard-coded time, another phage protein named holin is inserted in the cytoplasmic membrane leading to membrane disruption [1] enabling the lysin to access the peptidoglycan, thereby causing cell lysis and release of progeny phage [2]. Interestingly, exogenously applied recombinant lysins are able to cleave the integral peptidoglycan bonds of susceptible bacteria [3]. Non-phage bacteriolysins have been also described that are encoded by specific bacterial species and serve the purpose of lysing competing strains or autolysis at the septal region of the bacterial cell during cell division. Lysostaphin is a bacteriocin secreted by *Staphylococcus simulans* biovar *staphylolyticus* and directed against the cell wall of competing *S. aureus* [4]. The *S. aureus* autolysin (Atl) is a 138-kDa protein which is processed into two major peptidoglycan hydrolases and localizes on the cell wall at the septal region of an upcoming cell division site and plays a key role in cell separation [5]. Species-specific phages [6] and lysostaphin have been tested as potential therapeutics in numerous in vitro and in vivo studies [4, 7-10].

Phage lysins, lysostaphin, and autolysins all consist of a cell wall targeting (CWT) domain (or also known as cell wall binding domain; CBD) and one or more catalytic domains [4, 10-13]. CWTs recognize specific surface moieties, positioning the catalytic domain on the bacterial surface for enzymatic cleavage of the peptidoglycan. The catalytic domains are relatively conserved whereas CWTs are not conserved across species and impart species-specificity and can have variable binding affinities to different strains. Several studies reported the construction of truncated [8] or chimeric versions of phage lysins [7] showing that individual domains function when grafted into heterologous contexts such as green fluorescence protein (GFP). Lysostaphin CWT (GFP-CWT) was shown to bind to *S. aureus* as well as *P. sacculi* [9]. Similarly, GFP fusion of autolysin CWT binds to *S. aureus* with a dissociation constant of 15 nM [14]. Crystal structure studies show that Isolated CWTs have a compact structure and can fold independently. Thus, isolated CWT domain can be used to target heterologous proteins to the surface of bacteria at the site of infection.

Antibodies constitute the central pillar of the humoral immune response. Antibodies targeted against bacterial toxins capture and neutralize the toxins and as such can reduce the virulence of the respective bacterial species. However, antitoxin antibodies are not specifically targeted to the site of bacterial infection as they lack the ability to recognize bacterial cell wall. Antibodies that recognize bacterial surface antigens such as capsular polysaccharides and other surface moieties through their antigen binding Fab domains opsonize the bacteria allowing the innate immune response to bind and phagocytose the bacteria. This function is dependent on the Fc portion of the antibodies that undergo specific interaction with their receptors on the surface of phagocytic cells such as neutrophils or macrophages. The adaptive immune system requires prior encounter with the invading bacteria or a vaccine mimicking the respective bacteria to generate protective antibodies, a process that takes days to weeks before a fully functional protective response can be mounted. Therefore, active vaccination is useful after the onset of acute infections.

BRIEF SUMMARY

This disclosure provides a therapeutic polypeptide comprising a cell wall targeting domain of a Bacteriocin/phage/bacteriocin-like inhibitory substance (BLIS) fused to an immune function mediating component (IFMC), wherein the therapeutic polypeptide can target the IFMC to a bacterial target.

In certain aspects, the BLIS is selected from the group consisting of phage lysins, lysostaphin, autolysins, Bacteriocin AS-48, Bacteriocin ColE9, Phage phiKZ gp144, Phage O9882, Phage (YC), BLIS (*Vibrio harveyi* strain VIB 571), BLIS (FM1025), Lysostaphin, φNM3 lysin, φ11, lysine, φ68, P17, φB30, lysin, φK, LysK, φMR11, MV-L, adherence binding domain of the pilin protein, E-colicins, Autolysin, φSs2, PlySs2bacteriophage lysin (PlySs2), derived from a *Streptococcus suis* phage, Endolysins OBPgp279 (from *Pseudomonas fluorescens* phage OBP), PVP-SE1gp146 (*Salmonella enterica* serovar Enteritidis phage PVP-SE1), E201φ2-1gp229 (*Pseudomonas chlororaphis* phage 201φ2-1), Hybrid between FyuA binding domain of pesticin fused to the N-terminus of T4 lysozyme, phage endolysins, PlyL and PlyG, LambdaSa2 (λSa2) (cpl-7), lysogenic bacteriophage SM1 (Fibrinogen Binding Domain of Bacteriophage Lysin), Endolysin CD27L, mycobacteriophage Ms6, any cell-wall-targeting fragment thereof, and any combination thereof.

In certain aspects the IFMC comprises an antibody or fragment thereof, an antigen for which a human or animal host has pre-existing antibodies, an Fc receptor targeting domain, an opsonizing agent, an adjuvant, a TLR agonist, a cytokine, or a combination thereof. For example, the antibody or fragment thereof can be specific for a bacterial antigen, e.g., a toxin, e.g., a *Staphylococcus aureus* toxin such as a superantigen, a staphylococcal enterotoxin, a toxic shock syndrome toxin 1; TSST-1, an alpha hemolysin, a gamma hemolysin, a leukocidin, any fragment thereof, or any combination thereof, a *Clostridium difficile* toxin A (TcdA) and toxin B (TcdB), a *Clostridium perfringens* toxin, a *Bacillus anthracis* toxin, *Clostridium diphtheria* toxin, an *E. Coli* toxin, a *Pseudomonas aeruginosa* toxin, a *Vibrio cholerae* toxin, a *Klebsiella pneumoniae* toxin, a *Streptococcus pneumoniae* toxin such as a pneumolysin, an streptolysin, an *Enterococcus faecalis* toxin, a fragment thereof, or a combination thereof. In certain aspects the antibody or fragment thereof is not antigen-specific, but rather provides an effector function. In certain aspects, the antibody fragment comprises an Fc portion of an antibody lacking the Fab portion. In certain aspects the Fc portion is from a human IgG antibody, e.g., an IgG1 or an IgG3 antibody.

In certain aspects, the IFMC comprises an antigen such as a non-pathogenic variant of a bacterial toxin, e.g., a mutant of staphylococcal enterotoxin B (SEB), tetanus toxoid, pertussis toxoid, any fragment thereof, or any combination thereof. In certain aspects the IFMC comprises a viral protein such as an influenza hemagglutinin, any fragment thereof, or any combination thereof.

In certain aspects of the therapeutic polypeptide provided herein, the BLIS is fused to the IFMC through a linker. In certain aspects a therapeutic polypeptide as provided herein can further comprise a heterologous amino acid sequence, e.g., a His-tag, a ubiquitin tag, a NusA tag, a chitin binding domain, a B-tag, a HSB-tag, green fluorescent protein (GFP), a calmodulin binding protein (CBP), a galactose-binding protein, a maltose binding protein (MBP), cellulose binding domains (CBD's), an avidin/streptavidin/Strep-tag, trpE, chloramphenicol acetyltransferase, lacZ (β-Galactosidase), a FLAG™ peptide, an S-tag, a T7-tag, a fragment of any such heterologous peptide, or a combination of two or more heterologous peptides. In certain aspects the heterologous amino acid sequence encodes an immunogen, a T-cell epitope, a B-cell epitope, a fragment of any of said heterologous peptides, and a combination of two or more of said heterologous peptides.

This disclosure further provides an isolated polynucleotide comprising a nucleic acid which encodes a therapeutic polypeptide as described above. In certain aspects, the polynucleotide can further comprise a heterologous nucleic acid such as a promoter operably associated with the nucleic acid encoding the therapeutic polypeptide.

The disclosure further provides a vector, e.g., a plasmid vector comprising the provided polynucleotide, and a host cell, e.g., a bacterium such as *Escherichia coli*, an insect cell, a mammalian cell or a plant cell comprising the provided vector.

The disclosure further provides a method of producing a therapeutic polypeptide, comprising culturing a provided host cell, and recovering the therapeutic polypeptide.

The disclosure further provides a composition, e.g., a pharmaceutical composition comprising the therapeutic polypeptide provided herein, and a carrier.

The disclosure further provides a method for treating a bacterial infection, disease, or disorder, comprising administering to a subject in need of treatment an effective amount of the therapeutic polypeptide as provided herein, or a composition as provided herein. In certain aspects, the bacterial infection, disease, or disorder is a localized or systemic infection of skin, soft tissue, blood, or an organ. In certain aspects the disease is a respiratory disease such as pneumonia. In certain aspects the disease is sepsis. In certain aspects the subject is a mammal, e.g., a human, a bovine or a canine. In certain aspects the therapeutic polypeptide or composition can be administered via intramuscular injection, intradermal injection, intraperitoneal injection, subcutaneous injection, intravenous injection, oral administration, mucosal administration, intranasal administration, or pulmonary administration.

BRIEF DESCRIPTION OF THE DRAWINGS/FIGURES

FIG. 1A-B is an Infection Site Targeted Anti-toxin Antibody (ISTAb) Technology. A) Schematic of an ISTAb molecule. An anti-toxin monoclonal antibody (mAb) is genetically fused to a cell wall targeting domain of a bacteriolysin through a flexible linker sequence. B) ISTAb molecules accumulate at the site of infection by binding to the bacterial cell wall, capture the released toxins and the bacteria-toxin complex is cleared by polymorphonuclear cells (neutrophils; PMN) or other phagocytic cells.

Figure 2:
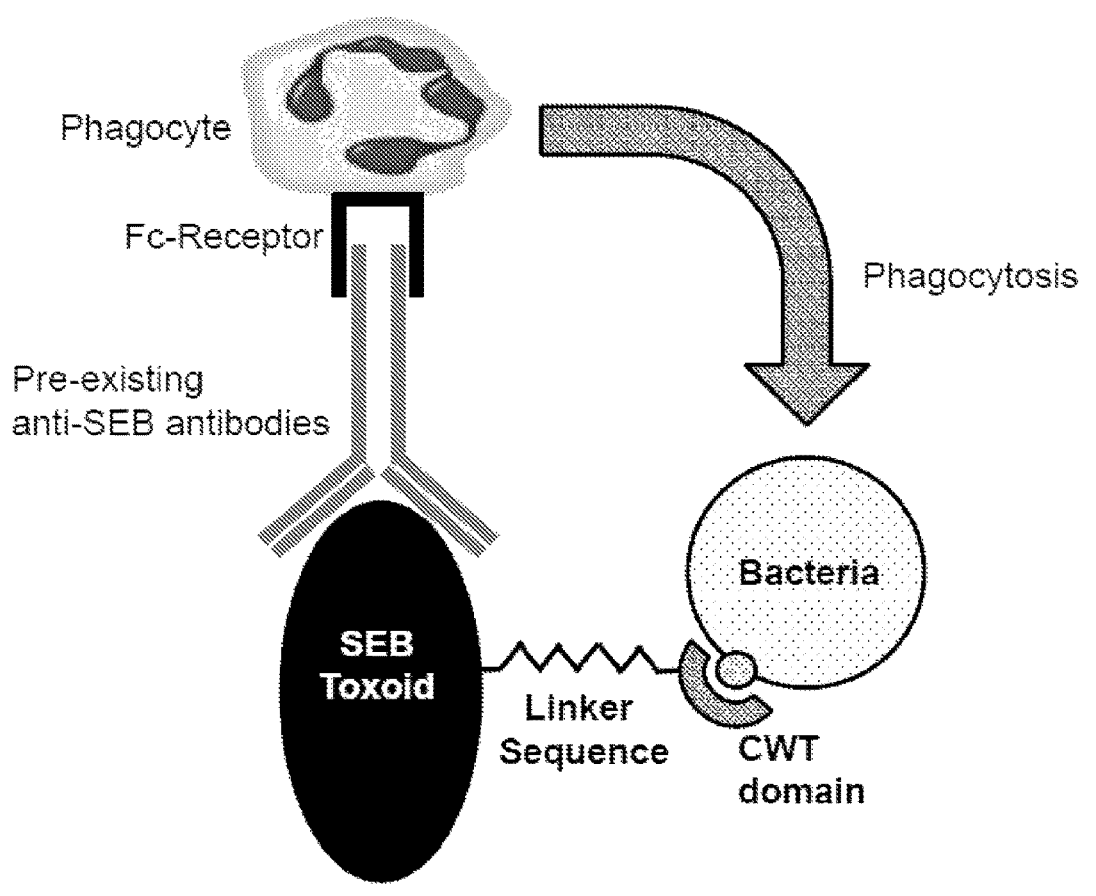

FIG. 2 is an Infection site targeted universal antigen (ISTUA). ISTUA is generated by fusing a specific CWT to an antigen such as detoxified staphylococcal enterotoxin B (SEB) for which most human hosts have pre-existing antibodies. Upon infection ISTUA is administered to patient. ISTUA is accumulated at the site of infection by binding to the bacteria through its CWT domain. The pre-existing antibodies bind to SEB and recruit the phagocytes leading to phagocytic clearance of the bacteria.

Figure 5:
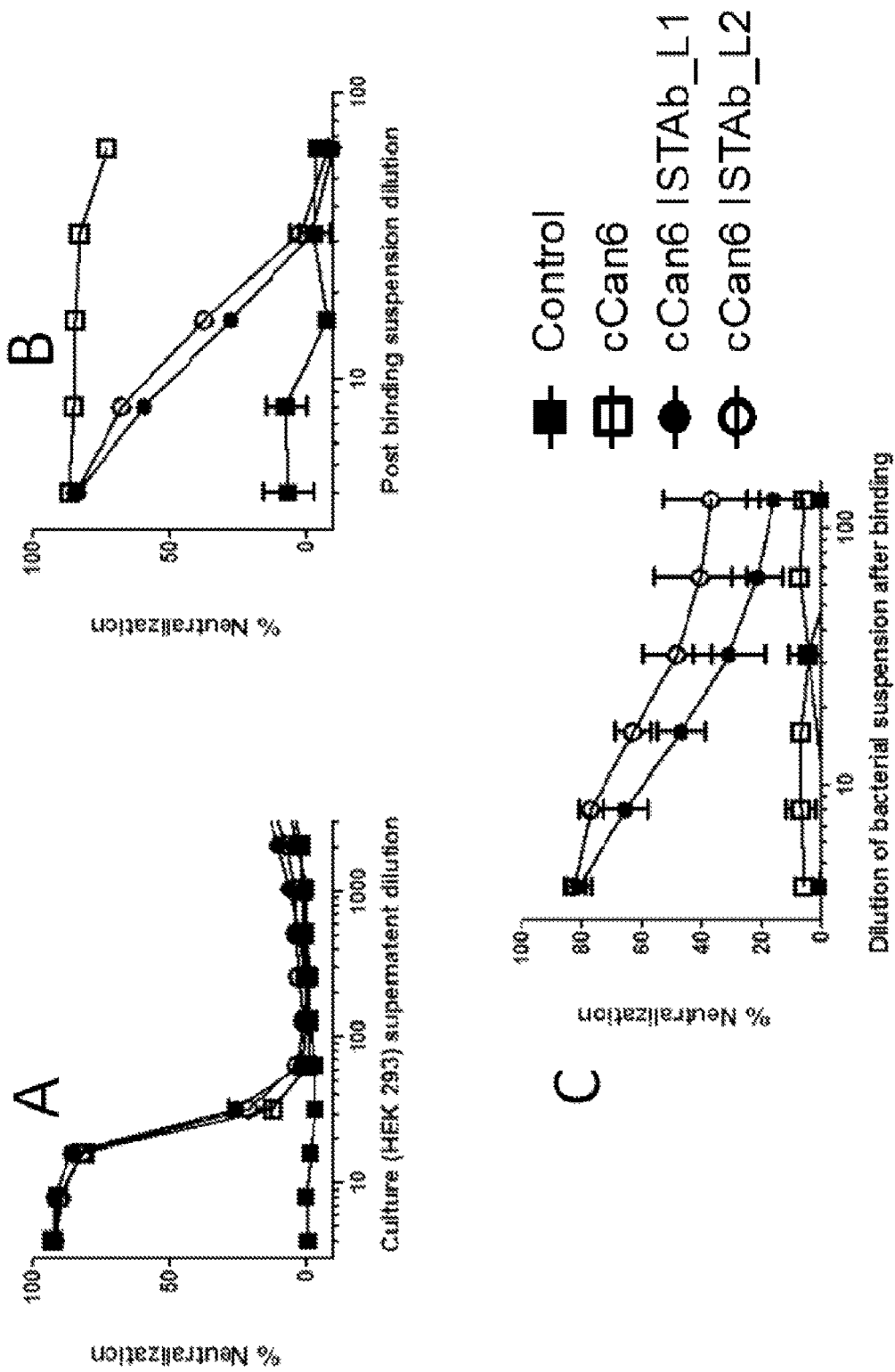

FIG. 5A-C shows in-vitro functional TNA for the constructs. A) Culture supernatant from different constructs grown in HEK293 cell-line were used in alpha toxin (0.15 ug/ml) neutralization assay (TNA) B) Supernatants were incubated with cell suspension made from overnight culture of NE286 (protein A null JE2 (USA300) strain). Suspensions were then centrifuged and TNAs were carried out in the supernatants. C) Pellets were used to carry alpha toxin TNAs.

Figure 6:
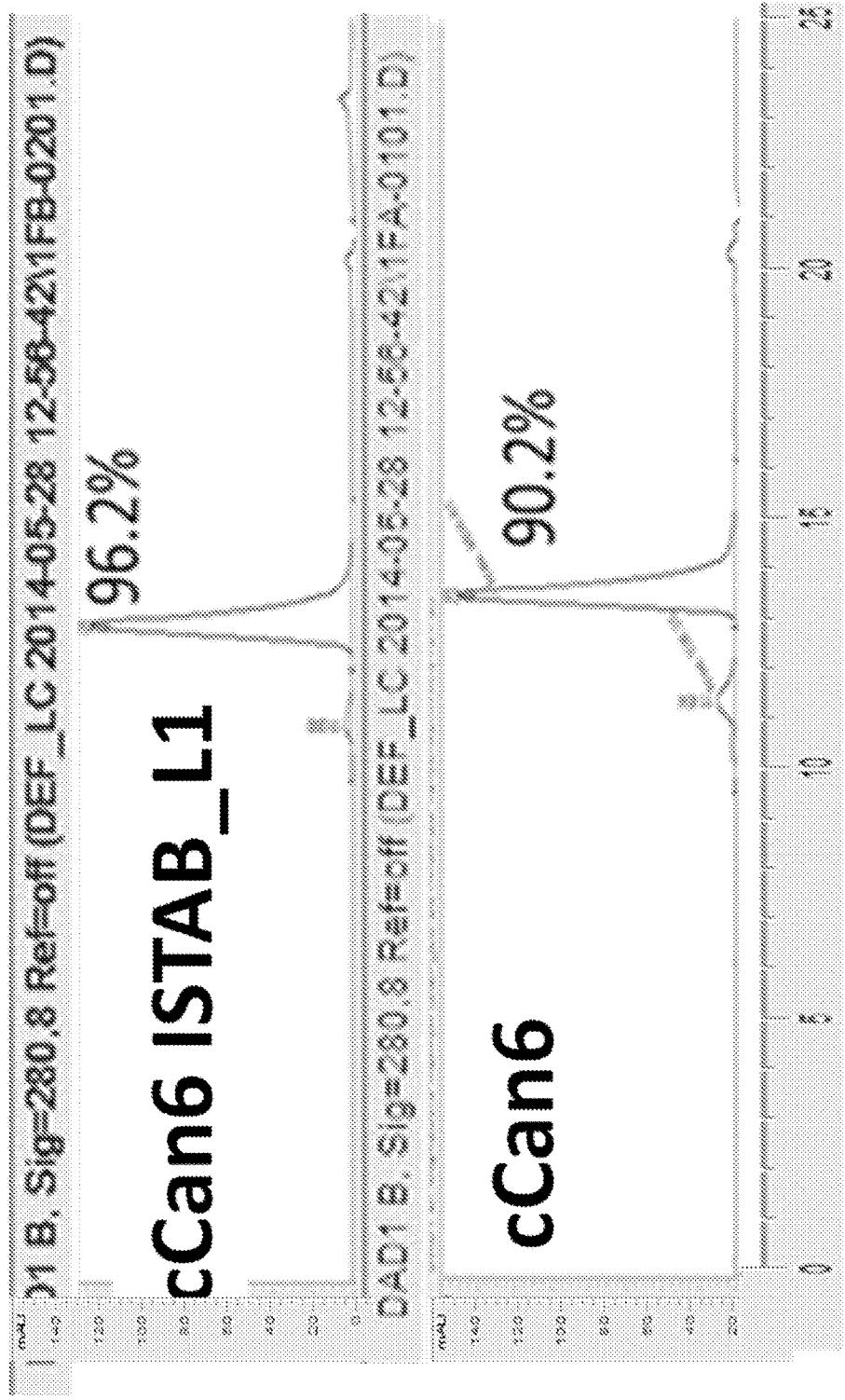

FIG. 6 shows HPLC analysis of cCan6 ISTAB_L1 and cCan 6.

DETAILED DESCRIPTION

Definitions

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The terms "nucleic acid" or "nucleic acid fragment" refers to any one or more nucleic acid segments, e.g., DNA or RNA fragments, present in a polynucleotide or construct. Two or more nucleic acids of the present invention can be present in a single polynucleotide construct, e.g., on a single plasmid, or in separate (non-identical) polynucleotide constructs, e.g., on separate plasmids. Furthermore, any nucleic acid or nucleic acid fragment can encode a single polypeptide, e.g., a single antigen, cytokine, or regulatory polypeptide, or can encode more than one polypeptide, e.g., a nucleic acid can encode two or more polypeptides. In addition, a nucleic acid can encode a regulatory element such as a promoter or a transcription terminator, or can encode a specialized element or motif of a polypeptide or protein, such as a secretory signal peptide or a functional domain.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349, 1997) comprising a polynucleotide. A polynucleotide can be provided in linear (e.g., mRNA), circular (e.g., plasmid), or branched form as well as double-stranded or single-stranded forms. A polynucleotide can comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, a "peptide," an "oligopeptide," a "dipeptide," a "tripeptide," a "protein," an "amino acid chain," an "amino acid sequence," or any other term used to refer to a chain or chains of two or more amino acids, are included in the definition of a "polypeptide," (even though each of these terms can have a more specific meaning) and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The terms "fragment," "analog," "derivative," or "variant" when referring to polypeptides provided herein include any polypeptides which retain at least some of the binding activity, immunogenicity or antigenicity of the parent protein. Fragments of a polypeptide provided herein can include, e.g., proteolytic fragments or deletion fragments. In certain aspects, fragments exhibit reduced pathogenicity when delivered to a subject.

The term "variant," as used herein, refers to a polypeptide that differs from the recited polypeptide due to amino acid substitutions, deletions, insertions, and/or modifications. Non-naturally occurring variants can be produced using art-known mutagenesis techniques. In some embodiments, variant polypeptides differ from an identified sequence by substitution, deletion or addition of three amino acids or fewer. Such variants can generally be identified by modifying an polypeptide sequence, and evaluating, e.g., the binding properties of the modified polypeptid.

Variants can also, or alternatively, contain other modifications, whereby, for example, a polypeptide can be conjugated or coupled, e.g., fused to a heterologous amino acid sequence, e.g., a signal (or leader) sequence at the N-terminal end of the protein which co-translationally or post-translationally directs transfer of the protein. The polypeptide can also be conjugated or produced coupled to a linker or other sequence for ease of synthesis, purification or identification of the polypeptide (e.g., 6-His), or to enhance binding of the polypeptide to a solid support.

As used herein, the term "antibody" (or a fragment, variant, or derivative thereof) refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like.

As indicated above, the variable region allows the binding molecule to selectively recognize and specifically bind epitopes on antigens. That is, the VL domain and VH domain, or a subset of the complementarity determining regions (CDRs), of an antibody combine to form the variable region that defines a three-dimensional antigen-binding site. This quaternary binding molecule structure forms the antigen-binding site present at the end of each arm of the Y. More specifically, the antigen-binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the cases where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196: 901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein.

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, or bispecific or multispecific antibodies. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that an antibody or fragment, variant, or derivative thereof binds to an epitope via its antigen-binding domain, and that the binding entails some complementarity between the antigen binding domain and the epitope. According to this definition, an antibody is said to "specifically bind" to an epitope when it binds to that epitope via its antigen-binding domain more readily than it would bind to a random, unrelated epitope.

An antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen-binding fragment to a given epitope by at least 90%, at least 80%, at least 70%, at least 60%, or at least 50%.

Antibodies or antigen-binding fragments, variants, or derivatives thereof disclosed herein can be described or specified in terms of the epitope(s) or portion(s) of an antigen, e.g., a target polypeptide that they recognize or specifically bind.

As used herein the terms "treat," "treatment," or "treatment of" (e.g., in the phrase "treating a patient having a bacterial infection, disease, or disorder") refers to reducing the potential for pathogenic bacterial pathology, or disease symptoms, reducing the extent of a bacterial infection, or clearing a pathogenic bacterial infection in a subject being treated. For example, treating can refer to the ability of a therapy when administered to a subject, to prevent a bacterial infection from occurring, prevent a bacterial infection from spreading, e.g., from the site of infection and/or to cure or to alleviate a bacterial disease symptoms, signs, or causes. Treating also refers to mitigating or decreasing at least one clinical symptom and/or inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

The present disclosure provides methods and systems providing therapeutic benefit in the treatment of bacterial infections, diseases, or disorders. A therapeutic benefit is not necessarily a cure for a particular infection, disease, or disorder, but rather encompasses alleviation of a bacterial infection, disease or disorder or increased survival, elimination of the bacterial infection, disease or disorder, reduction of a symptom associated with the bacterial infection, disease or disorder, prevention or alleviation of a secondary disease, disorder or condition resulting from the occurrence of a primary bacterial infection, disease or disorder, and/or prevention of the bacterial infection, disease or disorder.

The terms "subject" or "patient" as used herein refer to any subject, particularly a mammalian subject, for whom diagnosis, prognosis, or therapy of a bacterial infection, disease or disorder is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient having a bacterial infection, disease or disorder" includes subjects, such as mammalian subjects, that would benefit from the administration of a therapy and/or preventive treatment for that bacterial infection, disease or disorder.

The term "therapy" as used herein includes any means for curing, mitigating, or preventing a bacterial infection, disease or disorder, including, for example, therapeutic agents, instrumentation, supportive measures, and surgical or rehabilitative procedures. In this respect, the term therapy encompasses any protocol, method and/or therapeutic or diagnostic that can be used in prevention, management, treatment, and/or amelioration of a bacterial infection, disease or disorder. In some aspects, the term "therapy" refers to administering a therapeutically effective amount of a therapeutic agent that is capable of targeting the cell wall of a given bacterial species with a therapeutic agent.

The term "therapeutic agent" as used herein refers to any therapeutically active substance that is administered to a subject having a bacterial infection, disease or disorder to produce a desired, usually beneficial, effect. A therapeutic agent as provided herein comprises a bacterial cell-wall targeting domain from a bacteriocin/phage/bacteriocin-like inhibitory substance (BLIS), as described below and in Table 1, fused to a therapeutic moiety such as an antibody or fragment thereof, a toxoid or superantigen, or fragment thereof, or other agent, including, but not limited to peptides, protein drugs, protein conjugate drugs, enzymes, cytokines, ligands, etc.

A "therapeutically effective" amount as used herein is an amount of therapeutic agent that provides some improvement or benefit to a subject having a bacterial infection, disease or disorder. Thus, a "therapeutically effective"

amount is an amount that provides some alleviation, mitigation, and/or decrease in at least one clinical symptom of the bacterial infection, disease or disorder. Those skilled in the art will appreciate that the therapeutic effects need not be complete or curative, as long as some benefit is provided to the subject. In some aspects, the term "therapeutically effective" refers to an amount of a therapeutic agent therapeutic agent that is capable of clearing, reducing, or sequestering a bacterial infection, disease or disorder in a patient in need thereof.

As used herein, a "sufficient amount" or "an amount sufficient to" achieve a particular result in a patient having a bacterial infection, disease or disorder refers to an amount of a therapeutic agent (e.g., a CWT fusion protein as described herein) that is effective to produce a desired effect, which is optionally a therapeutic effect (i.e., by administration of a therapeutically effective amount).

Therapeutic Polypeptides

This disclosure provides a comprehensive approach to specifically target various immune functions, e.g., humoral immune functions, cellular immune functions, or cytokine-mediated immune functions, to the site of infection by a variety of therapeutic fusion proteins that comprise a bacteriolysin cell wall targeting domain (CWT) and an immune function mediating component (IFMC).

In certain aspects, the CWT is fused to the IFMC through a linker, e.g., a peptide linker. Suitable peptide linker sequences can be chosen based on their ability to adopt a flexible, extended conformation, or a secondary structure that could interact with joined polypeptides, or based on their ability to increase overall solubility of the fusion polypeptide, or based on their lack of electrostatic or water-interaction effects that influence joined peptide regions.

In certain aspects, a therapeutic polypeptide as provided herein can be attached to a heterologous polypeptide. Various heterologous polypeptides can be used, including, but not limited to an N- or C-terminal peptide imparting stabilization, secretion, or simplified purification, such as a hexa-Histidine-tag, a ubiquitin tag, a NusA tag, a chitin binding domain, ompT, ompA, pelB, DsbA, DsbC, c-myc, KSI, polyaspartic acid, (Ala-Trp-Trp-Pro)n, polyphenyalanine, polycysteine, polyarginine, a B-tag, a HSB-tag, green fluorescent protein (GFP), influenza virus hemagglutinin (HAI), a calmodulin binding protein (CBP), a galactose-binding protein, a maltose binding protein (MBP), a cellulose binding domains (CBD's), dihydrofolate reductase (DHFR), glutathione-S-transferase (GST), streptococcal protein G, staphylococcal protein A, T7gene10, an avidin/streptavidin/Strep-tag complex, trpE, chloramphenicol acetyltransferase, lacZ (β-Galactosidase), His-patch thioredoxin, thioredoxin, a FLAG™ peptide (Sigma-Aldrich), an S-tag, or a T7-tag. See, e.g., Stevens, R. C., Structure, 8:R177-R185 (2000). Heterologous polypeptides can also include any pre- and/or pro-sequences that facilitate the transport, translocations, processing and/or purification of a therapeutic polypeptide provided herein from a host cell or any useful immunogenic sequence, including but not limited to sequences that encode a T-cell epitope of a microbial pathogen, or other immunogenic proteins and/or epitopes.

The CWT targets the fusion protein to the bacterial surface leading to accumulation at the site of infection. The IFMC mediates various immune functions such as toxin neutralization or recruitment of immune cells that can clear the bacteria. Table 1 lists a number of potential CWTs from Phage lysins and other bacteriolysins that can be engineered for targeting immune functions to the site of infection.

TABLE 1

Examples of phage lysins that can be used to target immune functions to the site of infection through CWT (CBD) domains.

| Bacteriocin/phage/bacteriocin-like inhibitory substance (BLIS) | Cell wall targeting (CWT) domain | Activity against (specificity) | Ref. |
|---|---|---|---|
| Bacteriocin AS-48 | membrane-interacting peptide | Gram Positive and negative | [16] |
| Bacteriocin ColE9 | receptor binding domain | Gram Negative | [17, 18] |
| Phage phiKZ gp144 | C-terminal domain | *P. aeruginosa* | [19, 20] |
| Phage O9882 | Not defined | Broad range of clinical isolates of ESBL-producing *E. coli.* | [21] |
| Phage (YC) | Not defined | *Vibrio* | [22] |
| BLIS (*Vibrio harveyi* strain VIB 571) | Not defined | *Vibrio* | [23] |
| BLIS (FM1025) | Not defined | *Salmonella enteritidis* | [24] |
| Lysostaphin | aa 401-493 | *S. aureus* | [4, 9] |
| ϕ NM3 lysin | aa 158-291 | *S. aureus* | [10] |
| ϕ11, lysine | aa 370-490 | *S. aureus* | [25] |
| ϕ68, P17 | 25 C-terminal amino acids | *S. aureus* | [7, 26, 27] |
| ϕ B30, lysin | 354-443 | *S. aureus* | [26, 28] |
| ϕ K, LysK | 412-481 | *S. aureus* | [8] |
| ϕ MR11, MV-L | 322-481 | *S. aureus* | [29] |
| adherence binding domain of the pilin protein | chimeric proteins with N- or C-terminally fused pilin DSL peptides | *Pseudomonas aeruginosa* | [30] |
| E-colicins | Ala366-Arg399 of the helix-loop-helix | *Escherichia coli* | [31] |
| Autolysin | 2044-2536 | *S. aureus* | [11, 12, 14] |

TABLE 1-continued

Examples of phage lysins that can be used to target immune functions to the site of infection through CWT (CBD) domains.

| Bacteriocin/phage/ bacteriocin-like inhibitory substance (BLIS) | Cell wall targeting (CWT) domain | Activity against (specificity) | Ref. |
|---|---|---|---|
| ϕ Ss2, PlySs2bacteriophage lysin (PlySs2), derived from a *Streptococcus suis* phage | C-terminal SH3b binding domain (392-410) | MRSA, vancomycin-intermediate *S. aureus* (VISA), *Streptococcus suis, Listeria, Staphylococcus simulans, Staphylococcus epidermidis, Streptococcus equi*, *Streptococcus agalactiae* (group B *streptococcus* [GBS]), *S. pyogenes, Streptococcus sanguinis*, group G streptococci (GGS), group E streptococci (GES), and *Streptococcus pneumoniae* | [32] |
| Endolysins OBPgp279 (from *Pseudomonas fluorescens* phage OBP), | an N-terminal cell wall binding domain | *Pseudomonas* | [33] |
| PVP-SE1gp146 (*Salmonella enterica* serovar Enteritidis phage PVP-SE1) | N-terminal cell wall binding domain | *Salmonella* | [33] |
| E201φ2-1gp229 (*Pseudomonas chlororaphis* phage 201φ2-1) | N-terminal cell wall binding domain | *Pseudomonas* | [33] |
| Hybrid between FyuA binding domain of pesticin fused to the N-terminus of T4 lysozyme | FyuA binding domain of pesticin fused to the N-terminus of T4 lysozyme. | *Y. pestis* and *Y. pseudotuberculosis*, pathogenic *E. coli* | [34] |
| phage endolysins, PlyL and PlyG | C-terminal | *Bacillus anthracis* | [35] |
| LambdaSa2 (λSa2) (cpl-7) | C-terminal | *Streptococcus pyogenes, Streptococcus dysgalactiae, Streptococcus uberis, Streptococcus equi*, GES, and GGS | [36] |
| lysogenic bacteriophage SM1(Fibrinogen Binding Domain of Bacteriophage Lysin) | N-terminal | *S. pneumoniae* | [37] |
| Endolysin CD27L | C-terminal (180-270 aa) | *Clostridium difficile* | [38, 39] |
| mycobacteriophage Ms6 | N-terminal region of Gp1(lysin$_{384}$) | Mycobacteria | [40] |

In certain aspects, the IFMC can comprise an antibody or fragment thereof, e.g., an antigen-binding fragment or a non-antigen-binding fragment such as an Fc region, an antigen, e.g., a bacterial antigen such as a toxin mutant with reduced pathogenicity, an antigen to which the subject is expected to have an existing immune response, such as a super antigen (e.g., *staphylococcus* exotoxin B), *pseudomonas* exoproten A (EPA), toxoid antigens used in pediatric vaccines such as tetanus toxoid, pertussis toxoid, diphtheria toxoid, or a viral antigen derived from ubiquitous viruses such as influenza virus hemagglutinin, hepatitis virus B core antigen, antigens from Epstein-Barr Virus, measles, mumps, rubella, polyomavirus, or cytomegalovirus (CMV).

In other aspects, the IFMC can comprise of an immune-stimulatory molecule or adjuvant, such as flagellin, various ligands for toll-like receptors (TLR), a choleratoxin subunit, lipophilic immune stimulatory complexes (ISCOMS), a saponin, cytokines, co-stimulatory molecules such as CD28, fungal immunomodulatory protein (FIP), immune stimulating polysaccharides, or short antibacterial peptides such as alpha, beta, and theta defensins.

Examples of fusion proteins comprising a CWT include, but are not limited to, Infection site targeted anti-toxin antibodies (ISTAb), Anti-bacterial immune-redirecting vaccines, and Anti-bacterial spontaneous vaccines.

(1) Infection Site Targeted Anti-Toxin Antibodies (ISTAb):

Figure 1:
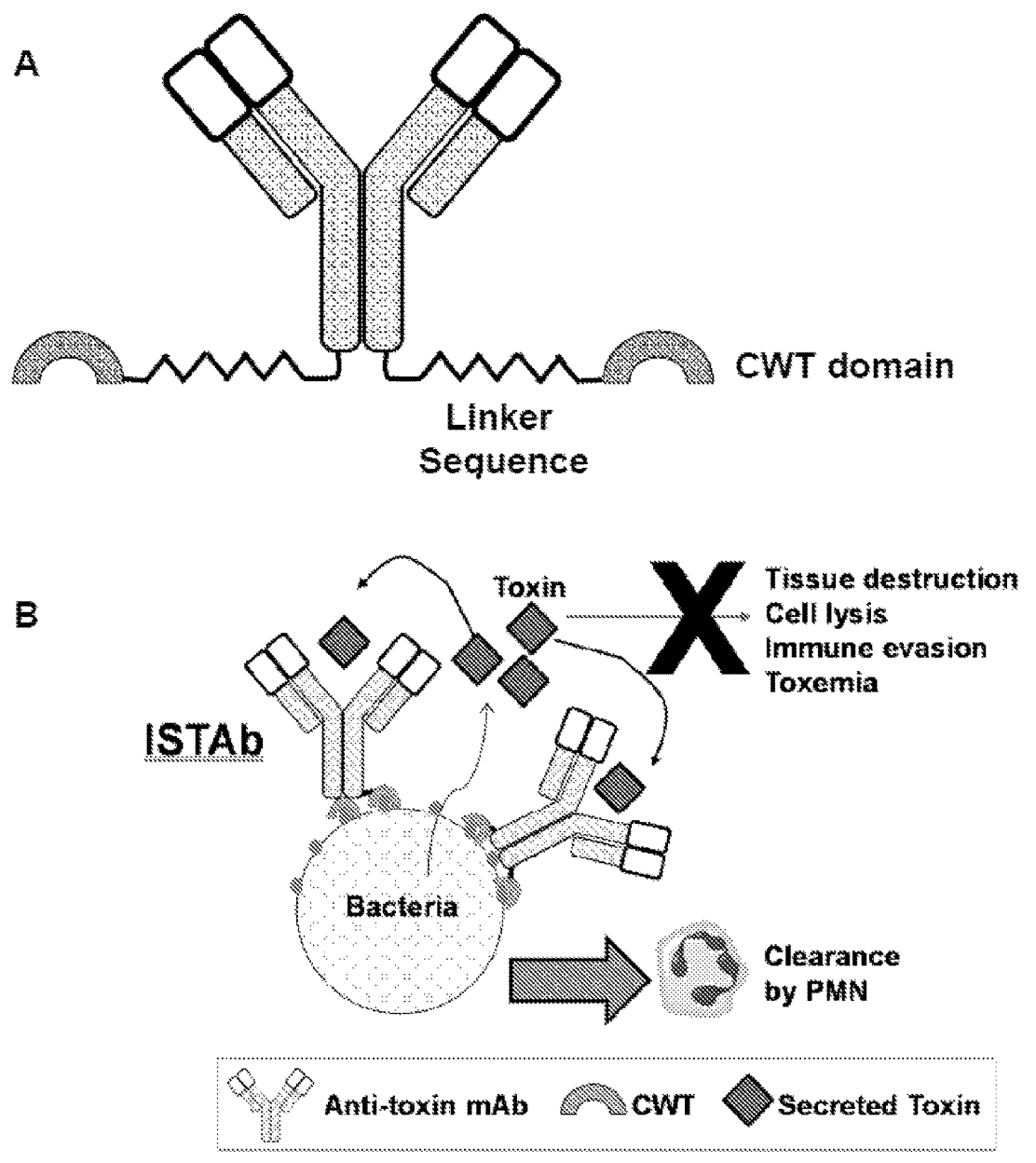

This technology takes advantage of high affinity and species specificity of bacteriolysin CWTs to target therapeutic antitoxin antibodies to the site of infection. An anti-toxin monoclonal antibody is genetically fused to the CWT of a specific bacteriolysin (FIG. 1A). The fusion protein is expressed in a host cell to produce the Infection Site Targeted antitoxin Antibodies (ISTAbs). ISTABs, when administered to an infected host, accumulate at the site of infection through binding to the cell wall of the invading bacteria, will capture the toxins and the whole bacteria-ISTAb-toxin complex is cleared by phagocytic cells of the host (FIG. 1B). ISTAbs can exhibit a number of favorable features including, but not limited to: i) specific and high affinity binding [15] to the infectious agent; ii) further enhancement of the binding by the avidity effect since each ISTAb will have two CWT domains, iii) accumulation at the site of infection where antitoxin is needed, iv) sequestration of the toxin at the site of infection preventing toxemia, and/or v) concurrent clearance of bacteria and toxin as the phagocytes engulf the bacteria, a process that may be even further enhanced by potential opsonic activity of ISTAbs.

ISTAbs can be used as therapeutic agents for treatment of a variety of bacterial infections where toxins play a critical role in pathogenesis. Non-limiting examples of such applications include:

*Staphylococcus aureus*: Neutralizing monoclonal antibodies against *S. aureus* toxins such as superantigens (staphylococcal enterotoxins and toxic shock syndrome toxin 1; TSST-1), alpha hemolysin, gamma hemolysins, or leukocidins are fused to CWT of *S. aureus* specific phage lysins, lysostaphin, or autolysin to target neutralizing activity to the site of infection for treatment of various *S. aureus* infections such as sepsis, pneumonia, osteomyelitis, and endocarditis.

*Clostridium difficile*: Neutralizing monoclonal antibodies against *C. difficile* toxin A (TcdA) and toxin B (TcdB) are fused to CWT of *C. difficile* specific phage lysins such as CD27L to target the antitoxin activity to the site of infection for treatment of *C. difficile* associated diarrhea (CAD).

Similar approaches can be devised for a variety of other bacterial species including but not limited to *C. perfringens*, *B. anthracis*, and *C. diphtheria*.

(2) Anti-Bacterial Immune-Redirecting Vaccines:

A second, non-limiting application of the technology is aimed at redirecting an existing, unrelated immune response to the site of a new bacterial infection leading to clearance of the bacteria. A CWT specific for the bacteria of interest (see Table 1) is fused to an antigen for which most human or animal hosts have pre-existing antibodies. FIG. 2 depicts an example of such fusion protein using a detoxified recombinant mutant of staphylococcal enterotoxin B (SEB). The recombinant toxoid is genetically fused to a CWT specific for the bacteria of interest through a flexible linker to generate an Infection Site Targeted Universal Antigen (ISTUA). The ISTUA can be used for treatment of an infected patient or animal upon which the molecules will accumulate at the site of infection. Pre-existing antibodies to the universal antigen (in this example SEB) can recognize the antigen and opsonize the bacteria as a result of specific binding to the antigen. This will trigger recruitment of phagocytes that bind to the Fc portion of the bound antibodies through their Fc receptor and phagocytosis of the bacteria leading to clearance of infection. Other examples of such universal antigens that can be used for creation of ISTUA include but are not limited to: tetanus toxoids, pertussis toxoids, and influenza hemagglutinin.

This approach can be used for rapid treatment of life threatening infections such as pneumonia or endocarditis upon identification of the infecting pathogen. In certain settings such as elective surgeries with high risk of infection the patients can be boosted with the antigen prior to surgery to enhance the response. After surgery infected patients can be treated with an ISTUA containing the antigen fused to the appropriate CWT specific for the identified pathogen.

(3) Anti-Bacterial Spontaneous Vaccines

Figure 3:
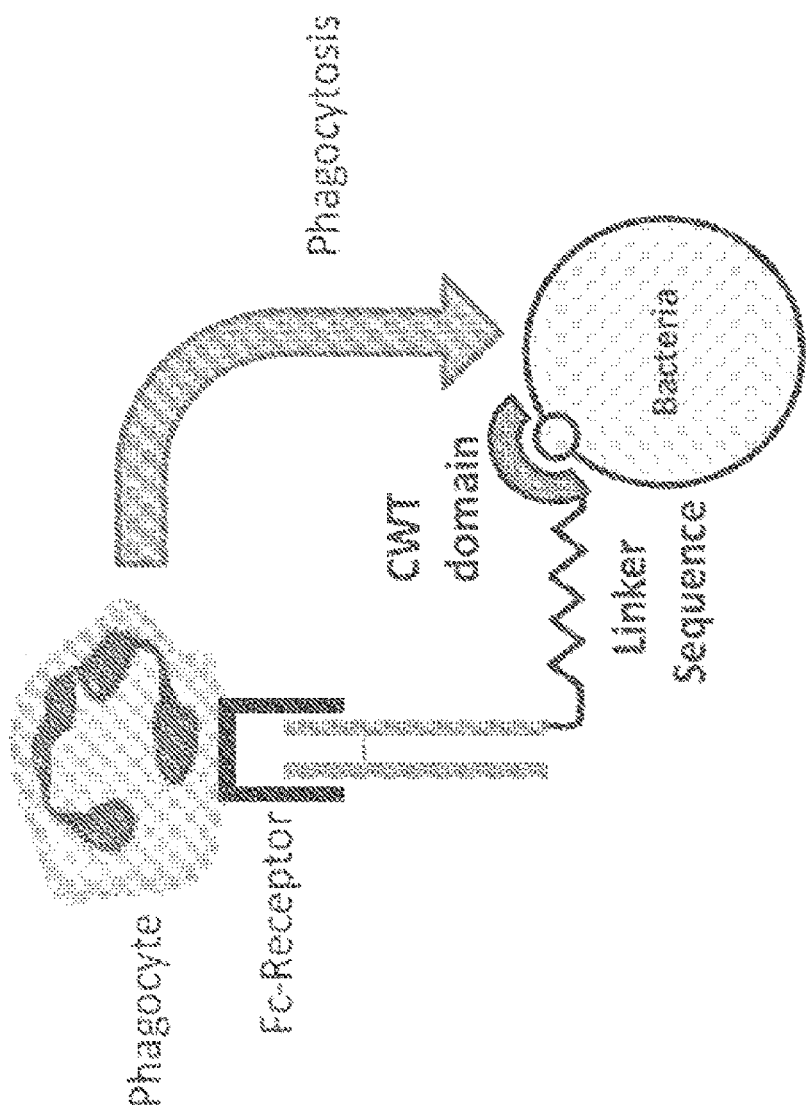
FIG. 3 is an Infection site targeted Fc molecule (ISTAF). ISTAF created by direct linkage of cell wall targeting domain to the Fc portion of an antibody targets the phagocytes to the site of bacterial infection leading to clearance of bacteria.

A third non-limiting application of the technology is a modified version of the ISTUA, described above. In this approach the CWT is fused to the Fc portion of a human IgG subtype such as IgG1 or IgG3 lacking the Fab portion. This fusion protein will be similarly accumulated at the site of infection and provide a direct link to phagocytes through the Fc receptor without the need for an indirect antibody mediated interaction. FIG. 3 depicts an example of an infection site targeted Fc molecule (ISTAF).

Polynucleotides

The present invention is further directed to an isolated polynucleotide comprising a nucleic acid encoding a therapeutic polypeptide as provided herein. In certain embodiments, an isolated polynucleotide provided herein can further comprise non-coding regions such as promoters, operators, or transcription terminators as described elsewhere herein. In some embodiments, a polynucleotide as described above can further comprise a heterologous nucleic acid. The heterologous nucleic acid can, in some embodiments, encode a heterologous polypeptide fused to a therapeutic polypeptide as provided herein. For example, an isolated polynucleotide of the invention can comprise additional coding regions encoding, e.g., a heterologous polypeptide fused to a therapeutic polypeptide as described above, or coding regions encoding heterologous polypeptides separate from a therapeutic polypeptide as described above such as, but not limited to, selectable markers, immune enhancers, and the like.

Also provided are expression constructs, vectors, and/or host cells comprising polynucleotides as provided herein. An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. In certain embodiments, the polynucleotide is "recombinant." Isolated polynucleotides or nucleic acids provided herein can be produced synthetically. The relative degree of purity of a polynucleotide or polypeptide of the invention is easily determined by well-known methods.

Vectors and Expression Systems

The present disclosure further provides a vector comprising a polynucleotide as provided herein. The term "vector," as used herein, refers to e.g., any of a number of nucleic acids into which a desired sequence can be inserted, e.g., by restriction and ligation, for transport between different genetic environments or for expression in a host cell. Nucleic acid vectors can be DNA or RNA. Vectors include, but are not limited to, plasmids, phage, phagemids, bacterial genomes, and virus genomes. A cloning vector is one which is able to replicate in a host cell, and which is further characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host bacterium or just a single time per host before the host reproduces by mitosis. In the case of phage, replication can occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. As used herein, the term "plasmid" refers to a circular, double-stranded construct made up of genetic material (i.e., nucleic acids), in which the genetic material is extrachromosomal and in some instances, replicates autonomously. A polynucleotide of the present invention can be in a circular or linearized plasmid or in any other sort of vector. Procedures for inserting a nucleotide sequence into a vector, e.g., an expression vector, and transforming or transfecting into an appropriate host cell and cultivating under conditions suitable for expression are generally known in the art.

In certain aspects, the disclosure provides a vector comprising a nucleic acid sequence encoding a therapeutic polypeptide as described herein. In certain embodiments the vector is an expression vector capable of expressing the therapeutic polypeptide in a suitable host cell. The term "expression vector" refers to a vector that is capable of expressing a polypeptide, i.e., the vector sequence contains the regulatory sequences required for transcription and translation of a polypeptide, including, but not limited to promoters, operators, transcription termination sites, ribosome binding sites, and the like. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression can involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in bacteria or in cell cultures. The selection of an appropriate host is deemed to be within the scope of those skilled in the art from the teachings herein. In certain embodiments, the host cell is a bacterium, e.g., E. coli.

Host cells are genetically engineered (infected, transduced, transformed, or transfected) with vectors of the invention. Thus, in one aspect the disclosure provides a host cell comprising a vector which contains a polynucleotide of the present invention. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

Bacterial host-expression vector systems include, but are not limited to, a prokaryote (e.g., E. coli), transformed with recombinant bacteriophage DNA, plasmid DNA or cosmid DNA. In some embodiments, the plasmids used with E. coli use the T7 promoter-driven system regulated by the Lad protein via IPTG induction. A large number of suitable vectors are known to those of skill in the art, and are commercially available. The following bacterial vectors are provided by way of example: pET (Novagen), pET28, pBAD, pTrcHIS, pBR322, pQE70, pQE60, pQE-9 (Qiagen), phagescript, psiXl74, pBluescript SK, pbsks, pNH8A, pNHl6a, pNH18A, pNH46A (Stratagene), ptrc99a, pKK223-3, pKK233-3, pDR540, pBR322, pPS10, RSF1010, pRIT5 (Pharmacia); pCR (Invitrogen); pLex (Invitrogen), and pUC plasmid derivatives.

A suitable expression vector contains regulatory sequences which can be operably joined to an inserted nucleotide sequence encoding a therapeutic polypeptide as provided herein. As used herein, the term "regulatory sequences" means nucleotide sequences which are necessary for or conducive to the transcription of an inserted sequence coding a therapeutic polypeptide by a host cell and/or which are necessary for or conducive to the translation by a host cell of the resulting transcript into the desired therapeutic polypeptide. Regulatory sequences include, but are not limited to, 5' sequences such as operators, promoters and ribosome binding sequences, and 3' sequences such as polyadenylation signals or transcription terminators. Regulatory sequences can also include enhancer sequences or upstream activator sequences.

Generally, bacterial vectors will include origins of replication and selectable markers, e.g., the ampicillin, tetracycline, kanamycin, resistance genes of E. coli, permitting transformation of the host cell and a promoter derived from a highly-expressed gene to direct transcription of a downstream structural sequence. Suitable promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, or inducible promoters like cadmium (pcad), and beta-lactamase (pbla).

Once an expression vector is selected, a polynucleotide as provided herein can be cloned downstream of the promoter, for example, in a polylinker region. The vector is transformed into an appropriate bacterial strain, and DNA is prepared using standard techniques. The orientation and DNA sequence of the polynucleotide as well as all other elements included in the vector, are confirmed using restriction mapping, DNA sequence analysis, and/or PCR analysis. Bacterial cells harboring the correct plasmid can be stored as cell banks.

Pharmaceutical Compositions

This disclosure further provides compositions, e.g., immunogenic or pharmaceutical compositions that contain an effective amount of a therapeutic polypeptide as provided herein, or a polynucleotide encoding a therapeutic polypeptide. Compositions can further comprise additional components, e.g., carriers, excipients or adjuvants.

Compositions can be formulated according to known methods. Suitable preparation methods are described, for example, in *Remington's Pharmaceutical Sciences,* 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the invention can be administered directly to the subject. The subjects to be treated can be animals; in particular, human subjects can be treated.

Carriers that can be used with compositions provided herein are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Certain compositions provided herein further include one or more adjuvants, a substance added to the composition to, for example, enhance, sustain, localize, or modulate an immune response to an immunogen. The term "adjuvant" refers to any material having the ability to (1) alter or increase the immune response to a particular antigen or (2) increase or aid an effect of a pharmacological agent. Any compound which can increase the expression, antigenicity or immunogenicity of the polypeptide is a potential adjuvant.

A great variety of materials have been shown to have adjuvant activity through a variety of mechanisms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant can also alter or modulate an immune response, for example, by changing a primarily humoral or $Th_2$ response into a primarily cellular, or $Th_1$ response. Immune responses to a given antigen can be tested by various immunoassays well known to those of ordinary skill in the art, and/or described elsewhere herein.

A wide number of adjuvants are familiar to persons of ordinary skill in the art, and are described in numerous references. Adjuvants which can be used in compositions according to the present invention include, but are not limited to: inert carriers, such as alum, bentonite, latex, and acrylic particles; incomplete Freund's adjuvant, complete Freund's adjuvant; aluminum-based salts such as aluminum hydroxide; calcium-based salts; silica or any TLR biological ligand(s). In one embodiment, the adjuvant is aluminum hydroxide (e.g., ALHDROGEL™ wet gel suspension). The amount of adjuvant, how it is formulated, and how it is administered all parameters which are well within the purview of a person of ordinary skill in the art.

In some embodiments, a composition of the invention further comprises a liposome or other particulate carrier, which can serve, e.g., to stabilize a formulation, to target the formulation to a particular tissue, such as lymphoid tissue, or to increase the half-life of the polypeptide composition. Such particulate carriers include emulsions, foams, micelles, insoluble monolayers, liquid crystals, phospholipid dispersions, lamellar layers, iscoms, and the like. In these preparations, a therapeutic polypeptide as provided herein can be incorporated as part of a liposome or other particle, or can be delivered in conjunction with a liposome. Liposomes for use in accordance with the invention can be formed from standard vesicle-forming lipids, which generally include neutral and negatively charged phospholipids and a sterol, such as cholesterol. A composition comprising a liposome or other particulate suspension as well as a therapeutic polypeptide as provided herein can be administered intravenously, locally, topically, etc. in a dose which varies according to, inter alia, the manner of administration, the polypeptide being delivered, and the stage of the disease being treated.

For aerosol or mucosal administration, a therapeutic polypeptide as provided herein can be supplied in finely divided form, optionally along with a surfactant and, propellant and/or a mucoadhesive, e.g., chitosan. The surfactant must, of course, be pharmaceutically acceptable, and in some embodiments soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, in some embodiments 0.25-5% by weight. The balance of the composition is ordinarily propellant, although an atomizer can be used in which no propellant is necessary and other percentages are adjusted accordingly. In some embodiments, a therapeutic polypeptide as provided herein can be incorporated within an aerodynamically light particle, such as those particles described in U.S. Pat. No. 6,942,868 or U.S. Pat. Pub. No. 2005/0008633. A carrier can also be included, e.g., lecithin for intranasal delivery.

Methods of Treatment/Prevention and Regimens

Also provided is a method of treating or preventing a bacterial infection, disease, or disorder in a subject comprising administering to a subject in need thereof a composition as described herein comprising a therapeutic polypeptide as provided herein, or polynucleotides, vectors, or host cells encoding same. In certain embodiments, the subject is a vertebrate, e.g., a mammal, e.g., a feline, e.g., canine, e.g., bovine, e.g., a primate, e.g., a human.

In some embodiments, a subject is administered a composition as described herein comprising a therapeutic polypeptide as provided herein, or polynucleotides, vectors, or host cells encoding same prophylactically, e.g., as a prophylactic treatment in a healthy animal prior to potential or actual exposure to a bacterial pathogen, e.g., before surgery or before dental work, thus preventing disease, alleviating symptoms, reducing symptoms, or reducing the severity of disease symptoms. In one embodiment the disease is a respiratory disease, e.g., pneumonia. In another embodiment, the disease is sepsis. Other diseases or conditions to be treated or prevented include, but are not limited to, skin infections, wound infections, endocarditis, bone and joint infections, osteomyelitis, and/or meningitis. One or more compositions, therapeutic polypeptides, polynucleotides, vectors, or host cells as provided herein can also be used to treat a subject already exposed to the bacterial pathogen or already suffering from a bacterial infection, disease, or disorder to further stimulate the immune system of the animal, thus reducing or eliminating the symptoms associated with that exposure. As defined herein, "treatment of an animal" refers to the use of one or more compositions, therapeutic polypeptides, polynucleotides, vectors, or host cells as provided herein to prevent, cure, retard, or reduce the severity of symptoms brought on by a bacterial infection, disease, or disorder in an animal, and/or result in no worsening of symptoms over a specified period of time. It is not required that any composition, therapeutic polypeptide, polynucleotide, vector, or host cell provided herein confer total protection against a bacterial infection, disease, or disorder or totally cure or eliminate all related symptoms.

In therapeutic applications, a composition, therapeutic polypeptide, or polynucleotide as provided herein is administered to a subject in an amount sufficient to elicit an effective anti-bacterial response, to cure or at least partially arrest symptoms and/or complications.

In certain embodiments, a composition of the present invention is delivered to a subject by methods described herein, thereby achieving an effective therapeutic effect. According to the disclosed methods, a composition can be administered by mucosal delivery, transdermal delivery, subcutaneous injection, intravenous injection, oral administration, pulmonary administration, intramuscular (i.m.) administration, or via intraperitoneal injection. Other suitable routes of administration include, but are not limited to intratracheal, transdermal, intraocular, intranasal, inhalation, intracavity, intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intra-arterial (i.e., into the heart atrium) and sub arachnoidal (i.e., into the sub arachnoid spaces of the brain) administration.

Any mode of administration can be used so long as the mode results in the delivery and/or expression of the desired therapeutic polypeptide in an amount sufficient to treat or prevent a bacterial infection, disease, or disorder as described herein. Administration can be by e.g., needle injection, or other delivery or devices known in the art.

EXAMPLES

Figure 4:
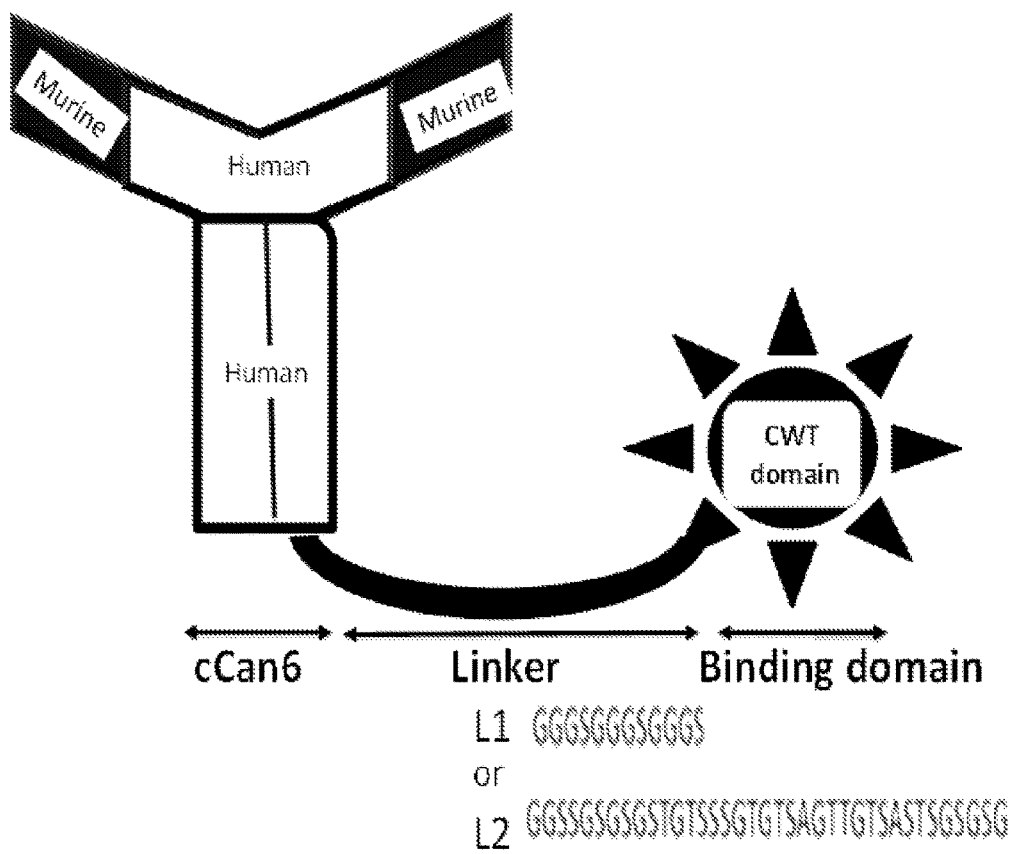
FIG. 4 is a schematic representation showing the cCan6 ISTAb_L1 and L2. cCan6 is a chimeric antibody which is derived by fusing variable region of sequenced Can6 mAb with constant region of Human light and heavy chain. cCan6 was then linked with lysostaphin CWT (binding domain) either by L1 or L2 to make cCan6_ISTAb_L1 and L2 respectively.

An infection site targeted antibody (ISTAb) was generated using an anti-alpha toxin (Hla) chimeric antibody named as "(cCan6)". The cell wall targeting domain (CWT) of lysostaphin (C-terminal 90 amino acids) was fused to the C-terminus of the anti-Hla mAb, (cCan6) using two different linkers denoted L1 and L2 (FIG. 4).

Biological activity of anti-Hla-ISTAbs was demonstrated comparing its activity to parental, cCan6 in an alpha toxin neutralizing rabbit RBC lysis assay. As seen in FIG. 5A, both parental antibody, cCan6 and ISTAbs, cCan6 ISTAb-L1 and ISTAb-L2 exhibited comparable bioactivity with toxin neutralizing titer of the supernatant dilution curve. These data clearly show that tethering the CWT to the antitoxin antibody does not interfere with the neutralizing activity of the monoclonal antibody.

Supernatants from transfected cells were also incubated with *S. aureus* followed by centrifugation to demonstrate binding of the ISTAb (and not the cCan6) to the bacteria as shown by reduced activity in the post-binding curves of ISTAbs and not the parental cCan6 (FIG. 5B). These data show that the cell wall binding activity of the isolated lysostaphin cell wall targeting domain is retained in the fusion ISTab.

Additionally, it was demonstrated that "cell-associated" ISTAbs upon binding to bacteria were still able to retain its toxin neutralizing ability. Briefly, cCan6 supernatant or cCan6-ISTAbs supernatant were incubated with *S. aureus*. Serial dilutions of pelleted bacteria were then added to the rabbit RBC lysis assay. As seen in FIG. 5C, cCan6-ISTAb_L1 and cCan6-ISTAb_L2 bound to bacteria retained its neutralizing activity. These data show that, ISTAb, when bound to the surface of bacteria, still retains its functional activity.

HPLC analysis was also performed on purified cCan6-ISTAb-L1 which showed >95% purity in the monomeric form (FIG. 6). Biacore-binding analysis showed comparable binding Kd values for anti-Hla parental cCan6 ($11\times10^{-9}$) and anti-cCan6-ISTAb-L1 ($8.3\times10^{-9}$). These data show that fusion of the antitoxin antibody with the CWT does not result in aggregation.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Roitt, I., Brostoff, J. and Male D., Immunology, 6$^{th}$ ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

REFERENCES

1. Wang, I. N.; Deaton, J.; Young, R., Sizing the holin lesion with an endolysin-beta-galactosidase fusion. *J Bacteriol* 2003, 185, (3), 779-87.
2. Wang, I. N.; Smith, D. L.; Young, R., Holins: the protein clocks of bacteriophage infections. *Annu Rev Microbiol* 2000, 54, 799-825.
3. Nelson, D.; Loomis, L.; Fischetti, V. A., Prevention and elimination of upper respiratory colonization of mice by group A streptococci by using a bacteriophage lytic enzyme. *Proc Natl Acad Sci USA* 2001, 98, (7), 4107-12.
4. Sabala, I.; Jonsson, I. M.; Tarkowski, A.; Bochtler, M., Anti-staphylococcal activities of lysostaphin and LytM catalytic domain. *BMC Microbiol* 2012, 12, 97.
5. Baba, T.; Schneewind, O., Targeting of muralytic enzymes to the cell division site of Gram-positive bacteria: repeat domains direct autolysin to the equatorial surface ring of *Staphylococcus aureus*. *EMBO J* 1998, 17, (16), 4639-46.
6. Vipra, A. A.; Desai, S. N.; Roy, P.; Patil, R.; Raj, J. M.; Narasimhaswamy, N.; Paul, V. D.; Chikkamadaiah, R.; Sriram, B., Antistaphylococcal activity of bacteriophage derived chimeric protein P128. *BMC Microbiol* 2012, 12, 41.
7. Manoharadas, S.; Witte, A.; Blasi, U., Antimicrobial activity of a chimeric enzybiotic towards *Staphylococcus aureus*. *J Biotechnol* 2009, 139, (1), 118-23.
8. Horgan, M.; O'Flynn, G.; Garry, J.; Cooney, J.; Coffey, A.; Fitzgerald, G. F.; Ross, R. P.; McAuliffe, O., Phage lysin LysK can be truncated to its CHAP domain and retain lytic activity against live antibiotic-resistant staphylococci. *Appl Environ Microbiol* 2009, 75, (3), 872-4.
9. Grundling, A.; Schneewind, O., Cross-linked peptidoglycan mediates lysostaphin binding to the cell wall envelope of *Staphylococcus aureus*. *J Bacteriol* 2006, 188, (7), 2463-72.
10. Daniel, A.; Euler, C.; Collin, M.; Chahales, P.; Gorelick, K. J.; Fischetti, V. A., Synergism between a novel chimeric lysin and oxacillin protects against infection by methicillin-resistant *Staphylococcus aureus*. *Antimicrob Agents Chemother* 2010, 54, (4), 1603-12.
11. Sivadon, V.; Rottman, M.; Quincampoix, J. C.; Prunier, E.; de Mazancourt, P.; Bernard, L.; Lortat-Jacob, A.; Piriou, P.; Judet, T.; Gaillard, J. L., Polymorphism of the cell wall-anchoring domain of the autolysin-adhesin AtlE and its relationship to sequence type, as revealed by multilocus sequence typing of invasive and commensal *Staphylococcus epidermidis* strains. *J Clin Microbiol* 2006, 44, (5), 1839-43.
12. Oshida, T.; Sugai, M.; Komatsuzawa, H.; Hong, Y. M.; Suginaka, H.; Tomasz, A., A *Staphylococcus aureus* autolysin that has an N-acetylmuramoyl-L-alanine amidase domain and an endo-beta-N-acetylglucosaminidase domain: cloning, sequence analysis, and characterization. *Proc Natl Acad Sci USA* 1995, 92, (1), 285-9.
13. Komatsuzawa, H.; Sugai, M.; Nakashima, S.; Yamada, S.; Matsumoto, A.; Oshida, T.; Suginaka, H., Subcellular localization of the major autolysin, ATL and its processed proteins in *Staphylococcus aureus*. *Microbiol Immunol* 1997, 41, (6), 469-79.
14. Ahmed, A. B.; Noguchi, K.; Asami, Y.; Nomura, K.; Fujii, H.; Sakata, M.; Tokita, A.; Noda, K.; Kuroda, A., Evaluation of cell wall binding domain of *Staphylococcus aureus* autolysin as affinity reagent for bacteria and its application to bacterial detection. *J Biosci Bioeng* 2007, 104, (1), 55-61.
15. Loessner, M. J.; Kramer, K.; Ebel, F.; Scherer, S., C-terminal domains of *Listeria monocytogenes* bacteriophage murein hydrolases determine specific recognition and high-affinity binding to bacterial cell wall carbohydrates. *Mol Microbiol* 2002, 44, (2), 335-49.
16. Cruz, V. L.; Ramos, J.; Melo, M. N.; Martinez-Salazar, J., Bacteriocin AS-48 binding to model membranes and pore formation as revealed by coarse-grained simulations. *Biochim Biophys Acta* 2013, 1828, (11), 2524-31.
17. Housden, N. G.; Wojdyla, J. A.; Korczynska, J.; Grishkovskaya, I.; Kirkpatrick, N.; Brzozowski, A. M.; Kleanthous, C., Directed epitope delivery across the *Escherichia coli* outer membrane through the porin OmpF. *Proc Natl Acad Sci USA* 2010, 107, (50), 21412-7.
18. Penfold, C. N.; Healy, B.; Housden, N. G.; Boetzel, R.; Vankemmelbeke, M.; Moore, G. R.; Kleanthous, C.; James, R., Flexibility in the receptor-binding domain of the enzymatic colicin E9 is required for toxicity against *Escherichia coli* cells. *J Bacteriol* 2004, 186, (14), 4520-7.
19. Paradis-Bleau, C.; Cloutier, I.; Lemieux, L.; Sanschagrin, F.; Laroche, J.; Auger, M.; Garnier, A.; Levesque, R. C., Peptidoglycan lytic activity of the *Pseudomonas aeruginosa* phage phiKZ gp144 lytic transglycosylase. *FEMS Microbiol Lett* 2007, 266, (2), 201-9.
20. Sycheva, L. V.; Shneider, M. M.; Sykilinda, N. N.; Ivanova, M. A.; Miroshnikov, K. A.; Leiman, P. G., Crystal structure and location of gp131 in the bacteriophage phiKZ virion. *Virology* 2012, 434, (2), 257-64.
21. Wang, J.; Hu, B.; Xu, M.; Yan, Q.; Liu, S.; Zhu, X.; Sun, Z.; Tao, D.; Ding, L.; Reed, E.; Gong, J.; Li, Q. Q.; Hu, J., Therapeutic effectiveness of bacteriophages in the rescue of mice with extended spectrum beta-lactamase-producing *Escherichia coli* bacteremia. *Int J Mol Med* 2006, 17, (2), 347-55.
22. Cohen, Y.; Joseph Pollock, F.; Rosenberg, E.; Bourne, D. G., Phage therapy treatment of the coral pathogen *Vibrio coralliilyticus*. *Microbiologyopen* 2013, 2, (1), 64-74.
23. Prasad, S.; Morris, P. C.; Hansen, R.; Meaden, P. G.; Austin, B., A novel bacteriocin-like substance (BUIS) from a pathogenic strain of *Vibrio harveyi*. *Microbiology* 2005, 151, (Pt 9), 3051-8.
24. Portrait, V.; Cottenceau, G.; Pons, A. M., A *Fusobacterium* mortiferum strain produces a bacteriocin-like substance(s) inhibiting *Salmonella enteritidis*. *Lett Appl Microbiol* 2000, 31, (2), 115-7.
25. Sass, P.; Bierbaum, G., Lytic activity of recombinant bacteriophage phi11 and phi12 endolysins on whole cells and biofilms of *Staphylococcus aureus*. *Appl Environ Microbiol* 2007, 73, (1), 347-52.
26. Fritz, S. A.; Tiemann, K. M.; Hogan, P. G.; Epplin, E. K.; Rodriguez, M.; Al-Zubeidi, D. N.; Bubeck Wardenburg, J.; Hunstad, D. A., A serologic correlate of protective immunity against community-onset *Staphylococcus aureus* infection. *Clin Infect Dis* 2013, 56, (11), 1554-61.
27. Takac, M.; Blasi, U., Phage P68 virion-associated protein 17 displays activity against clinical isolates of *Staphylococcus aureus*. *Antimicrob Agents Chemother* 2005, 49, (7), 2934-40.
28. Donovan, D. M.; Dong, S.; Garrett, W.; Rousseau, G. M.; Moineau, S.; Pritchard, D. G., Peptidoglycan hydrolase fusions maintain their parental specificities. *Appl Environ Microbiol* 2006, 72, (4), 2988-96.

29. Rashel, M.; Uchiyama, J.; Ujihara, T.; Uehara, Y.; Kuramoto, S.; Sugihara, S.; Yagyu, K.; Muraoka, A.; Sugai, M.; Hiramatsu, K.; Honke, K.; Matsuzaki, S., Efficient elimination of multidrug-resistant *Staphylococcus aureus* by cloned lysin derived from bacteriophage phi MR11. *J Infect Dis* 2007, 196, (8), 1237-47.

30. Hahn, H.; Lane-Bell, P. M.; Glasier, L. M.; Nomellini, J. F.; Bingle, W. H.; Paranchych, W.; Smit, J., Pilin-based anti-*Pseudomonas* vaccines: latest developments and perspectives. *Behring Inst Mitt* 1997, (98), 315-25.

31. Mohanty, A. K.; Bishop, C. M.; Bishop, T. C.; Wimley, W. C.; Wiener, M. C., Enzymatic E-colicins bind to their target receptor BtuB by presentation of a small binding epitope on a coiled-coil scaffold. *J Biol Chem* 2003, 278, (42), 40953-8.

32. Gilmer, D. B.; Schmitz, J. E.; Euler, C. W.; Fischetti, V. A., Novel bacteriophage lysin with broad lytic activity protects against mixed infection by *Streptococcus pyogenes* and methicillin-resistant *Staphylococcus aureus*. *Antimicrob Agents Chemother* 2013, 57, (6), 2743-50.

33. Walmagh, M.; Briers, Y.; dos Santos, S. B.; Azeredo, J.; Lavigne, R., Characterization of modular bacteriophage endolysins from Myoviridae phages OBP, 201phi2-1 and PVP-SE1. *PLoS One* 2012, 7, (5), e36991.

34. Lukacik, P.; Barnard, T. J.; Keller, P. W.; Chaturvedi, K. S.; Seddiki, N.; Fairman, J. W.; Noinaj, N.; Kirby, T. L.; Henderson, J. P.; Steven, A. C.; Hinnebusch, B. J.; Buchanan, S. K., Structural engineering of a phage lysin that targets gram-negative pathogens. *Proc Natl Acad Sci USA* 2012, 109, (25), 9857-62.

35. Ganguly, J.; Low, L. Y.; Kamal, N.; Saile, E.; Forsberg, L. S.; Gutierrez-Sanchez, G.; Hoffmaster, A. R.; Liddington, R.; Quinn, C. P.; Carlson, R. W.; Kannenberg, E. L., The secondary cell wall polysaccharide of *Bacillus anthracis* provides the specific binding ligand for the C-terminal cell wall-binding domain of two phage endolysins, PlyL and PlyG. *Glycobiology* 2013, 23, (7), 820-32.

36. Diez-Martinez, R.; de Paz, H.; Bustamante, N.; Garcia, E.; Menendez, M.; Garcia, P., Improving the lethal effect of cpl-7, a pneumococcal phage lysozyme with broad bactericidal activity, by inverting the net charge of its cell wall-binding module. *Antimicrob Agents Chemother* 2013, 57, (11), 5355-65.

37. Seo, H. S.; Sullam, P. M., Characterization of the fibrinogen binding domain of bacteriophage lysin from *Streptococcus mitis*. *Infect Immun* 2011, 79, (9), 3518-26.

38. Mayer, M. J.; Narbad, A.; Gasson, M. J., Molecular characterization of a *Clostridium difficile* bacteriophage and its cloned biologically active endolysin. *J Bacteriol* 2008, 190, (20), 6734-40.

39. Mayer, M. J.; Garefalaki, V.; Spoerl, R.; Narbad, A.; Meijers, R., Structure-based modification of a *Clostridium difficile*-targeting endolysin affects activity and host range. *J Bacteriol* 2011, 193, (19), 5477-86.

40. Catalao, M. J.; Gil, F.; Moniz-Pereira, J.; Pimentel, M., The endolysin-binding domain encompasses the N-terminal region of the mycobacteriophage Ms6 Gp1 chaperone. *J Bacteriol* 2011, 193, (18), 5002-6.

EMBODIMENTS

Embodiment 1

A therapeutic polypeptide comprising a cell wall targeting domain of a Bacteriocin/phage/bacteriocin-like inhibitory substance (BLIS) fused to an immune function mediating component (IFMC), wherein the therapeutic polypeptide can target the IFMC to a bacterial target.

Embodiment 2

The therapeutic polypeptide of embodiment 1, wherein the BLIS is selected from the group consisting of phage lysins, lysostaphin, autolysins, Bacteriocin AS-48, Bacteriocin ColE9, Phage phiKZ gp144, Phage 09882, Phage (YC), BLIS (*Vibrio harveyi* strain VIB 571), BLIS (FM1025), Lysostaphin, ϕNM3 lysin, ϕ11, lysine, ϕ68, P17, ϕB30, lysin, ϕK, LysK, ϕMR11, MV-L, adherence binding domain of the pilin protein, E-colicins, Autolysin, ϕSs2, PlySs2bacteriophage lysin (PlySs2), derived from a *Streptococcus suis* phage, Endolysins OBPgp279 (from *Pseudomonas fluorescens* phage OBP), PVP-SE1gp146 (*Salmonella enterica* serovar *Enteritidis* phage PVP-SE1), E201φ2-1gp229 (*Pseudomonas chlororaphis* phage 201φ2-1), Hybrid between FyuA binding domain of pesticin fused to the N-terminus of T4 lysozyme, phage endolysins, PlyL and PlyG, LambdaSa2 (XSa2) (cpl-7), lysogenic bacteriophage SM1 (Fibrinogen Binding Domain of Bacteriophage Lysin), Endolysin CD27L, mycobacteriophage Ms6, any cell-wall-targeting fragment thereof, and any combination thereof.

Embodiment 3

The therapeutic polypeptide of embodiment 1 or embodiment 2, wherein the IFMC comprises an antibody or fragment thereof, an antigen for which a human or animal host has pre-existing antibodies, an Fc receptor targeting domain, an opsonizing agent, an adjuvant, a TLR agonist, a cytokine, an immune-stimulatory molecule such as flagellin, various ligands for toll-like receptors (TLR), a choleratoxin subunit, lipophilic immune stimulatory complexes (ISCOMS), a saponin, co-stimulatory molecules such as CD28, fungal immunomodulatory protein (FIP), immune stimulating polysaccharides, short antibacterial peptides such as alpha, beta, and theta defensins, fragments thereof, or a combination thereof.

Embodiment 4

The therapeutic polypeptide of embodiment 3, wherein the antibody or fragment thereof is specific for a bacterial antigen.

Embodiment 5

The therapeutic polypeptide of embodiment 4, wherein the bacterial antigen is a toxin.

Embodiment 6

The therapeutic polypeptide of embodiment 5, wherein the toxin comprises a *Staphylococcus aureus* toxin, a *Clostridium difficile* toxin A (TcdA) and toxin B (TcdB), a *Clostridium perfringens* toxin, a *Bacillus anthracis* toxin, a *Clostridium diphtheria* toxin, a *pseudomonas* exoproten A (EPA), a toxoid antigen such as tetanus toxoid, pertussis toxoid, diphtheria toxoid, or a viral antigen such as influenza virus hemagglutinin, hepatitis virus B core antigen, antigens from Epstein-Barr Virus, measles, mumps, rubella, polyomavirus, or cytomegalovirus (CMV). a fragment thereof, or a combination thereof.

Embodiment 7

The therapeutic polypeptide of embodiment 6, wherein the *Staphylococcus aureus* toxin comprises a superantigen, a staphylococcal enterotoxin, a toxic shock syndrome toxin 1; TSST-1, an alpha hemolysin, a gamma hemolysin, a leukocidin, any fragment thereof, or any combination thereof.

Embodiment 8

The therapeutic polypeptide of embodiment 3, wherein the antigen a non-pathogenic variant of a bacterial toxin, a viral protein, any fragment thereof, or any combination thereof.

Embodiment 9

The therapeutic polypeptide of embodiment 8, wherein the non-pathogenic variant of a bacterial toxin comprises a mutant of mutant of staphylococcal enterotoxin B (SEB), tetanus toxoid, pertussis toxoid, *pseudomonas* exoproten A (EPA), any fragment thereof, or any combination thereof.

Embodiment 10

The therapeutic polypeptide of embodiment 8, wherein the viral protein comprises an influenza hemagglutinin hepatitis virus B core antigen, antigens from Epstein-Barr Virus, measles, mumps, rubella, polyomavirus, or cytomegalovirus (CMV).

Embodiment 11

The therapeutic polypeptide of embodiment 3, wherein the antibody or fragment thereof comprises an Fc portion of an antibody lacking the Fab portion.

Embodiment 12

The therapeutic polypeptide of embodiment 11, comprising the Fc portion of a human IgG antibody.

Embodiment 13

The therapeutic polypeptide of embodiment 12, wherein the human IgG is an IgG1 or an IgG3.

Embodiment 14

The therapeutic polypeptide of any one of embodiments 1 to 13, wherein the BLIS is fused to the IFMC through a linker.

Embodiment 15

The therapeutic polypeptide of any one of embodiments 1 to 14 further comprising a heterologous amino acid sequence.

Embodiment 16

The therapeutic polypeptide of embodiment 15, wherein the heterologous amino acid sequence encodes a peptide selected from a group consisting of a His-tag, a ubiquitin tag, a NusA tag, a chitin binding domain, a B-tag, a HSB-tag, green fluorescent protein (GFP), a calmodulin binding protein (CBP), a galactose-binding protein, a maltose binding protein (MBP), cellulose binding domains (CBD's), an avidin/streptavidin/Strep-tag, trpE, chloramphenicol acetyltransferase, lacZ (β-Galactosidase), a FLAG™ peptide, an S-tag, a T7-tag, a fragment of any of said heterologous peptides, and a combination of two or more of said heterologous peptides.

Embodiment 17

The therapeutic polypeptide of embodiment 16, wherein the heterologous amino acid sequence encodes an immunogen, a T-cell epitope, a B-cell epitope, a fragment of any of said heterologous peptides, and a combination of two or more of said heterologous peptides.

Embodiment 18

An isolated polynucleotide comprising a nucleic acid which encodes the therapeutic polypeptide of any one of embodiments 1 to 17.

Embodiment 19

The polynucleotide of embodiment 18, further comprising a heterologous nucleic acid.

Embodiment 20

The polynucleotide of embodiment 19, wherein said heterologous nucleic acid comprises a promoter operably associated with the nucleic acid encoding the therapeutic polypeptide.

Embodiment 21

A vector comprising the polynucleotide of any one of embodiments 18 to 20.

Embodiment 22

The vector of embodiment 21, which is a plasmid.

Embodiment 23

The vector of embodiment 22, wherein said plasmid is a pET24 plasmid.

Embodiment 24

A host cell comprising the vector of any one of embodiments 21 to 23.

Embodiment 25

The host cell of embodiment 24, which is a bacterium, an insect cell, a mammalian cell or a plant cell.

Embodiment 26

The host cell of embodiment 25 wherein the bacterium is *Escherichia coli*.

Embodiment 27

A method of producing a therapeutic polypeptide, comprising culturing the host cell of any one of embodiments 24 to 26, and recovering the therapeutic polypeptide.

Embodiment 28

A composition comprising the therapeutic polypeptide of any one of embodiments 1 to 17 and a carrier.

Embodiment 29

The composition of embodiment 28, further comprising an adjuvant.

Embodiment 30

The composition of embodiment 29, wherein the adjuvant is alum or aluminum hydroxide.

Embodiment 31

A method for treating a bacterial infection, disease, or disorder, comprising administering to a subject in need of treatment an effective amount of the therapeutic polypeptide of any one of embodiments 1 to 17, or the composition of any one of embodiments 28 to 30.

Embodiment 32

The method of embodiment 31, wherein the bacterial infection, disease, or disorder is a localized or systemic infection of skin, soft tissue, blood, or an organ.

Embodiment 33

The method of embodiment 31 or embodiment 32, wherein the disease is a respiratory disease.

Embodiment 34

The method of embodiment 33, wherein the respiratory disease is pneumonia.

Embodiment 35

The method of embodiment 31 or embodiment 32, wherein the disease is sepsis.

Embodiment 36

The method of any one of embodiments 31 to 35, wherein the subject is
Embodiment a mammal.

Embodiment 37

The method of embodiment 36, wherein the mammal is a human.

Embodiment 38

The method of embodiment 36, wherein the mammal is bovine or canine.

Embodiment 39

The method of any one of embodiments 31 to 38, wherein the therapeutic polypeptide or composition is administered via intramuscular injection, intradermal injection, intraperitoneal injection, subcutaneous injection, intravenous injection, oral administration, mucosal administration, intranasal administration, or pulmonary administration.

What is claimed is:

1. A therapeutic polypeptide comprising a cell wall targeting (CWT) domain of a bacteriolysin fused to an immune function mediating component (IFMC) through a peptide linker:
   wherein the bacteriolysin is a bacteriocin selected from the group consisting of: Lysostaphin, Bacteriocin AS-48, Bacteriocin ColE9, adherence binding domain DSL peptides of the pilin protein, an E-colicin, Autolysin, and the FyuA binding domain of pesticin fused to the N-terminus of T4 lysozyme, or
   wherein the bacteriolysin is a phage encoded lysin selected from the group consisting of: Phage phiKZ gp144 lysin, φNM3 lysin, φ11 lysin, φ68 P17 lysin, φB30 lysin, φK LysK lysin, φMR11 MV-L lysin, φSs2 PlySs2bacteriophage lysin, OBPgp279 endolysin, PVP-SE1gp146 lysin, E201φ2-1gp229 lysin, Endolysin PlyL, Endolysin PlyG, LambdaSa2 cpl-7 lysin, bacteriophage SM1 lysin, Endolysin CD27L, and mycobacteriophage Ms6 lysin,
   wherein the IFMC comprises an antibody or antigen binding fragment thereof to a bacterial toxin or toxoid, or a fragment thereof, wherein the antibody or antigen binding fragment thereof lacks the ability to recognize a bacterial cell wall, and wherein the CWT domain of the therapeutic polypeptide can target the IFMC to a bacterial target.

2. The therapeutic polypeptide of claim 1, wherein the bacterial toxin or toxoid comprises a *Staphylococcus aureus* toxin, a *Clostridium difficile* toxin A (TcdA), a *Clostridium difficile* toxin B (TcdB), a *Clostridium perfringens* toxin, a *Bacillus anthracis* toxin, a *Clostridium* diphtheria toxin, an *E. coli* toxin, a *Pseudomonas* exoprotein A (EPA) or other *Pseudomonas aeruginosa* toxin, a *Vibrio cholerae* toxin, a *Klebsiella pneumoniae* toxin, a pneumolysin or other *Streptococcus pneumoniae* toxin, a streptolysin, an *Enterococcus faecalis* toxin, a tetanus toxoid, a pertussis toxoid, a diphtheria toxoid, or a fragment thereof.

3. The therapeutic polypeptide of claim 2, wherein the *Staphylococcus aureus* toxin comprises a superantigen, a staphylococcal enterotoxin, a toxic shock syndrome toxin 1 (TSST-1), an alpha hemolysin, a gamma hemolysin, a leukocidin, or any fragment thereof, or any combination thereof.

4. The therapeutic polypeptide of claim 1 further comprising a heterologous amino acid sequence.

5. The therapeutic polypeptide of claim 4, wherein the heterologous amino acid sequence encodes an immunogen, a T-cell epitope, a B-cell epitope, a fragment of any of said heterologous peptides, and a combination of two or more of said heterologous peptides.

6. The therapeutic polypeptide of claim 1, wherein the bacteriolysin is the bacteriocin Lysostaphin and the bacterial toxin is a *Staphylococcus aureus* alpha hemolysin toxin, or a toxoid and/or fragment thereof.

7. The therapeutic polypeptide of claim 1, wherein the bacteriolysin is the phage encoded lysin Endolysin PlyL and the bacterial toxin is a *Bacillus anthracis* toxin, or a toxoid and/or fragment thereof.

8. The therapeutic polypeptide of claim 1, wherein the bacteriolysin is the phage encoded Endolysin CD27L and the bacterial toxin is a *Clostridium difficile* toxin A (TcdA), or a toxoid and/or fragment of TcdA.

9. The therapeutic polypeptide of claim 1, wherein the bacteriolysin is the phage encoded lysin Endolysin PlyG and the bacterial toxin is a *Bacillus anthracis* toxin, or a toxoid and/or fragment thereof.

10. The therapeutic polypeptide of claim 1, wherein the bacteriolysin is the phage encoded Endolysin CD27L and the bacterial toxin is a *Clostridium difficile* toxin B (TcdB), or a toxoid and/or fragment of TcdB.

11. The therapeutic polypeptide of claim 1, wherein the bacteriolysin is the phage encoded ϕSs2 PlySs2bacteriophage lysin, and the bacterial toxin is a pneumolysin, or a toxoid and/or fragment thereof.

12. The therapeutic polypeptide of claim 1, wherein the bacteriolysin is the phage encoded bacteriophage SM1 lysin, and the bacterial toxin is a pneumolysin, or a toxoid and/or fragment thereof.

13. The therapeutic polypeptide of claim 1, wherein the bacteriolysin is the phage encoded ϕSs2 PlySs2bacteriophage lysin, and the bacterial toxin is a *Streptococcus pneumoniae* toxin other than a pneumolysin, or a toxoid and/or fragment thereof.

14. The therapeutic polypeptide of claim 1, wherein the bacteriolysin is the phage encoded bacteriophage SM1 lysin, and the bacterial toxin is a *Streptococcus pneumoniae* toxin other than a pneumolysin, or a toxoid and/or fragment thereof.

15. A composition comprising the therapeutic polypeptide of claim 1 and a carrier.

16. The composition of claim 15, further comprising an adjuvant.

17. The composition of claim 16, wherein the adjuvant is alum or aluminum hydroxide.

18. An isolated polynucleotide comprising a nucleic acid which encodes the therapeutic polypeptide claim 1.

19. The polynucleotide of claim 18, further comprising a heterologous nucleic acid.

20. The polynucleotide of claim 19, wherein said heterologous nucleic acid comprises a promoter operably associated with the nucleic acid encoding the therapeutic polypeptide.

21. A vector comprising the polynucleotide of claim 18.

22. The vector of claim 21, which is a plasmid.

23. The vector of claim 22, wherein said plasmid is a pET24 plasmid.

24. An isolated host cell comprising the vector of claim 21.

25. The isolated host cell of claim 24, which is a bacterium, an insect cell, a mammalian cell or a plant cell.

26. The isolated host cell of claim 25 wherein the bacterium is *Escherichia coli*.

27. A method of producing a therapeutic polypeptide, comprising culturing the isolated host cell of claim 24 and recovering the therapeutic polypeptide.

* * * * *